United States Patent
Bae et al.

(10) Patent No.: US 10,640,708 B2
(45) Date of Patent: *May 5, 2020

(54) LIQUID CRYSTAL COMPOSITION AND LIQUID CRYSTAL DISPLAY DEVICE INCLUDING THE SAME

(71) Applicant: Samsung Display Co. Ltd., Yongin-si, Gyeonggi-do (KR)

(72) Inventors: Ji Hong Bae, Yongin-si (KR); Keun Chan Oh, Hwaseong-si (KR); Seul Gee Lee, Seoul (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 104 days.

This patent is subject to a terminal disclaimer.

(21) Appl. No.: 15/400,199

(22) Filed: Jan. 6, 2017

(65) Prior Publication Data

US 2017/0292074 A1   Oct. 12, 2017

(30) Foreign Application Priority Data

Apr. 8, 2016 (KR) .................. 10-2016-0043216
Jul. 29, 2016 (KR) .................. 10-2016-0097115

(51) Int. Cl.
*C09K 19/32* (2006.01)
*C09K 19/30* (2006.01)
(Continued)

(52) U.S. Cl.
CPC ............ *C09K 19/32* (2013.01); *C07D 307/80* (2013.01); *C09K 19/3066* (2013.01);
(Continued)

(58) Field of Classification Search
None
See application file for complete search history.

(56) References Cited

U.S. PATENT DOCUMENTS 5,102,578 A * 4/1992 Buchecker .............. C07C 35/21
                                                    252/299.01
2013/0183460 A1* 7/2013 Klasen-Memmer ........................
                                                    C09K 19/062
                                                    428/1.4
2018/0010045 A1* 1/2018 Bae .................... C09K 19/3405

FOREIGN PATENT DOCUMENTS

CN   100415730 C    9/2008
DE   19900517 A1 * 7/1999 ........... C07D 307/79
(Continued)

OTHER PUBLICATIONS

English translation of DE19900517. (Year: 1999).*
(Continued)

*Primary Examiner* — Cynthia H Kelly
*Assistant Examiner* — Anna Malloy
(74) *Attorney, Agent, or Firm* — Cantor Colburn LLP

(57) ABSTRACT

A liquid crystal composition, comprising, at least one compound represented by Formula 1-A:

Formula 1-A

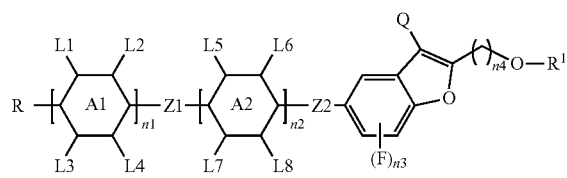

wherein, in the Formula 1-A, R—*, R¹—*, Q-*, *—Z1-*, *—Z2-*, (Continued)

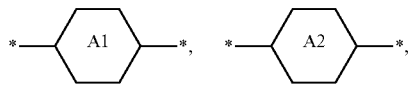

n1, n2, n3, n4, L1-*, L2-*, L3-*, L4-*, L5-*, L6-*, L7-*, and L8-* are the same as defined in the specification, and * is defined as a bonding site to a neighboring atom.

15 Claims, 5 Drawing Sheets

(51) Int. Cl.
    *C07D 307/80* (2006.01)
    *C09K 19/56* (2006.01)
    *G02F 1/1337* (2006.01)
    *G02F 1/1343* (2006.01)
    *G02F 1/1368* (2006.01)
    *C09K 19/12* (2006.01)
    *C09K 19/34* (2006.01)

(52) U.S. Cl.
    CPC ............ *C09K 19/56* (2013.01); *G02F 1/1368* (2013.01); *G02F 1/133723* (2013.01); *G02F 1/134309* (2013.01); *C09K 2019/122* (2013.01); *C09K 2019/124* (2013.01); *C09K 2019/301* (2013.01); *C09K 2019/3004* (2013.01); *C09K 2019/3009* (2013.01); *C09K 2019/3016* (2013.01); *C09K 2019/3408* (2013.01); *G02F 2001/133726* (2013.01)

(56) References Cited

FOREIGN PATENT DOCUMENTS

| | | |
|---|---|---|
| DE | 19900517 A1 | 7/1999 |
| DE | 19909761 A1 | 10/1999 |
| DE | 10-2004-053279 A1 | 6/2005 |
| EP | 19909760 A1 | 10/1999 |
| JP | 2003-509507 A | 3/2003 |
| WO | 2001-21606 A1 | 3/2001 |
| WO | WO-0121606 A1 * | 3/2001 ........... C07D 307/79 |

OTHER PUBLICATIONS

Extended European Search Report dated May 8, 2017, issued for the European Patent Application No. 16196728.6-1375.
Detlef Pauluth et al. "Advanced liquid crystals for television" J. Mater. Chem. 2004, 14, 1219-1227.

* cited by examiner

LIQUID CRYSTAL COMPOSITION AND LIQUID CRYSTAL DISPLAY DEVICE INCLUDING THE SAME

This application claims priority to Korean Patent Application No. 10-2016-0043216, filed on Apr. 8, 2016, and Korean Patent Application No. 10-2016-0097115, filed on Jul. 29, 2016, and all benefits accruing therefrom under 35 U.S.C. § 119, the contents of which are incorporated herein in their entirety by reference.

BACKGROUND

1. Field

The present disclosure relates to a liquid crystal composition and a liquid crystal display device including the same.

2. Description of the Related Art

A liquid crystal display device, which is one of the most widely used display devices, includes two substrates provided with field generating electrodes, such as a pixel electrode and a common electrode, and a liquid crystal layer disposed between the two substrates.

With the expansion of application field of the liquid crystal display device, it is desired to improve characteristics, such as response speed, contrast, drive voltage, and the like. In order to improve these characteristics, the liquid crystal compound contained in a liquid crystal composition needs low rotational viscosity, high chemical and physical stability, high liquid crystal phase-isotropic phase transition temperature, low liquid crystal phase lower limit temperature, appropriate elastic modulus, and the like. For high-speed response characteristics, a liquid crystal material having low rotational viscosity is required. Thus, there remains a need in liquid crystal display devices having improved properties.

SUMMARY

Aspects of the present disclosure provide a low-viscosity liquid crystal composition having high reliability and a liquid crystal display device including the same.

However, aspects of the present disclosure are not restricted to the one set forth herein. The above and other aspects of the present disclosure will become more apparent to one of ordinary skill in the art to which the present disclosure pertains by referencing the detailed description of the present disclosure given below.

According to an exemplary embodiment, there is provided a liquid crystal composition, including: at least one compound represented by Formula 1-A:

wherein, in the Formula 1-A,

R—* is *—H, *—F, *—Cl, *—Br, *—I, a $C_{1-12}$ alkyl group, or a cyano group, and $R^1$—* is a $C_{1-12}$ alkyl group;

Q-* is *—H or a $C_{1-5}$ alkyl group;

*—Z1-* and *—Z2-* are the same or different and are each independently *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_m$—* (wherein m is an integer of 1 to 5), *—CH=CH—*, *—CF=CF—*, *—CH=CF—*, *—CF=CH—*, *—C≡C—*, *—CH=CHCH$_2$O—*, or a single bond;

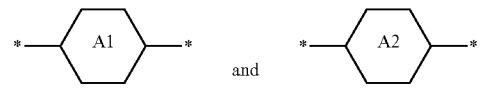 and are the same or different and are each independently

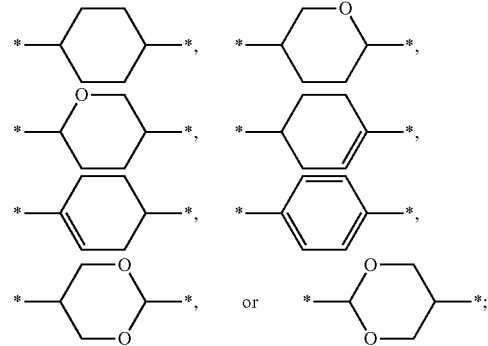

n1 and n2 are each independently an integer of 0 to 3;

n3 is an integer of 1 to 3;

n4 is an integer of 1 or 2; and

L1-*, L2-*, L3-*, L4-*, L5-*, L6-*, L7-*, and L8-* are the same or different and are each independently *—H, *—F, *—Cl, *—OCF$_3$, *—CF$_3$, *—CH$_2$F, or *—CHF$_2$.

In the Formula 1-A,

Q-* may be *—H, and n4 may be an integer of 1.

In the Formula 1-A,

Q-* may be *—H, and n3 may be an integer of 2.

Formula 1-A

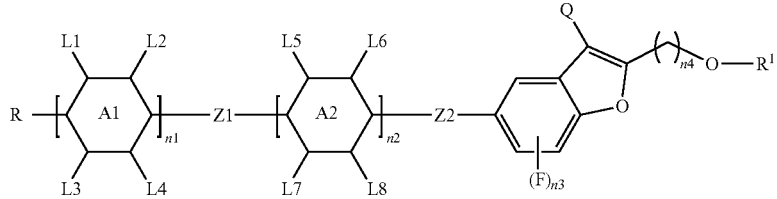

In the Formula 1-A,

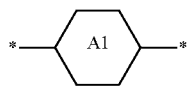 and 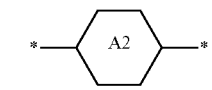

may be the same or different and may each independently be

 or 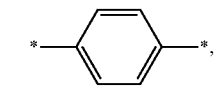, and
*—Z1-* and *—Z2-* may each be a single bond.

In an exemplary embodiment, the at least one compound represented by Formula 1-A may be a compound represented by Formula 1-B:

Formula 1-B

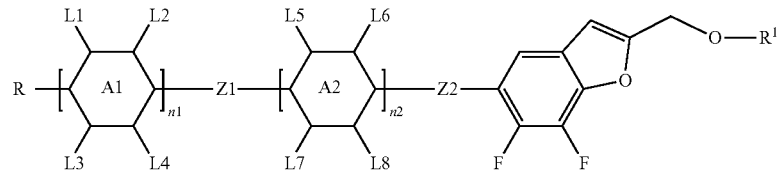

wherein, in the Formula 1-B,
A1, A2, L1-*, L2-*, L3-*, L4-*, L5-*, L6-*, L7-*, L8-*, R—*, R¹—*, *—Z1-*, *—Z2-*, n1, and n2 are the same as in the Formula 1-A.

In an exemplary embodiment, the at least one compound represented by Formula 1-A may be a compound represented by Formulae 1-1 to 1-4:

Formula 1-1

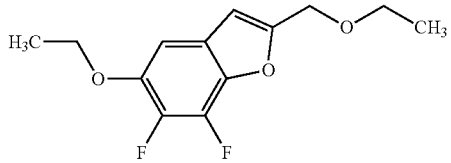

Formula 1-2

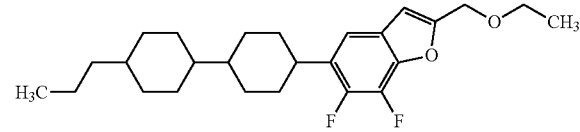

Formula 1-3

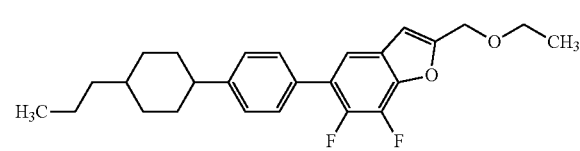

Formula 1-4

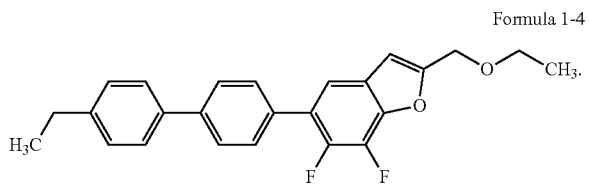

In an exemplary embodiment, the liquid crystal composition may further include at least one compound represented by Formulae 2-1 to 2-17:

Formula 2-1

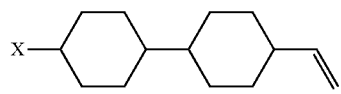

-continued

Formula 2-2

Formula 2-3

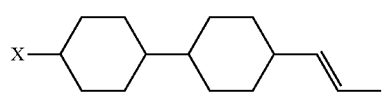

Formula 2-4

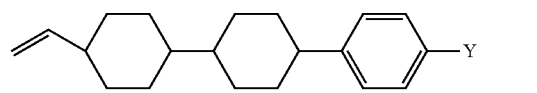

Formula 2-5

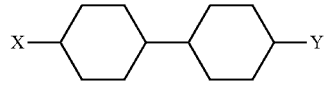

Formula 2-6

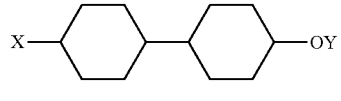

Formula 2-7

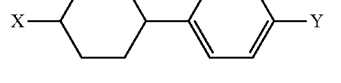

Formula 2-8

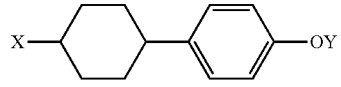

Formula 2-9
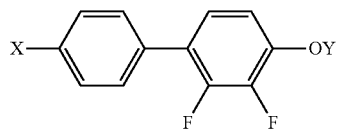

Formula 2-10
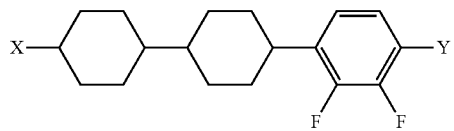

Formula 2-11
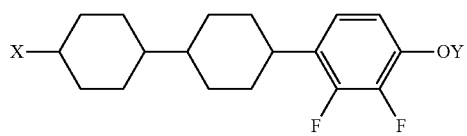

Formula 2-12
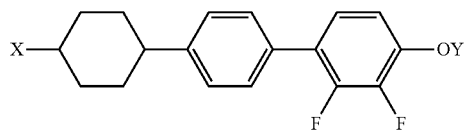

Formula 2-13
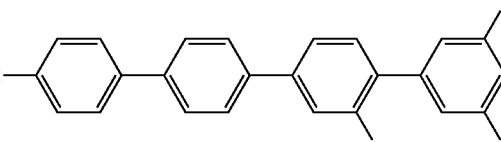

Formula 2-14
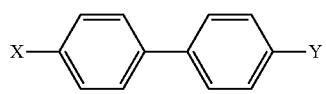

Formula 2-15
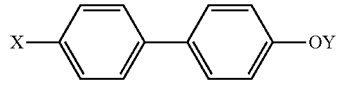

Formula 2-16
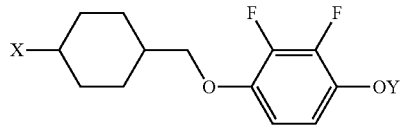

Formula 2-17
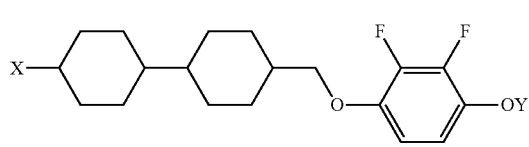

wherein, in the Formulae 2-1 to 2-17,

X—* and Y—* are each independently a $C_{1-5}$ alkyl group.

In an exemplary embodiment, the content of at least one compound represented by Formula P may be 0 percent by weight:

Formula P wherein, in the Formula P,

L11-*, L21-*, L31-*, L41-*, L51-*, L61-*, L71-*, L81-*, L91-*, L101-*, L111-*, and L121-* are the same or different and are each independently H—* or F—*; and R11-* and R12-* are the same or different and are each independently a $C_{1-5}$ alkyl group or a $C_{1-5}$ alkoxy group.

In an exemplary embodiment, the liquid crystal composition may have a refractive index anisotropy (Δn) of 0.08 to 0.12, a dielectric anisotropy (Δε) of −2.8 to −5.5, and a rotational viscosity (γ1, 20° C.) of 70 millipascal seconds (mPa)·s to 140 millipascal seconds (mPa·s).

In an exemplary embodiment, the content of the at least one compound represented by Formula 1-A may be about 1 percent by weight to about 10 percent by weight based on the total weight of the liquid crystal composition.

In an exemplary embodiment, the liquid crystal composition may further include at least one reactive mesogen represented by Formula RM:

P1-SP1-MG-SP2-P2        Formula RM wherein, in the Formula RM,

P1-* and P2-* are the same or different and are each independently

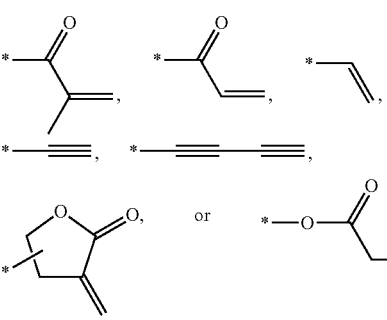

*—SP1-* is

*—[L—Z—L—Ar]$_a$—L—*

(wherein a is an integer of 0 to 2);

*—PS2-* is

*—L—[Ar—L—Z—L]$_b$—*

(wherein b is integer of 0 to 2);

*-MG-* is

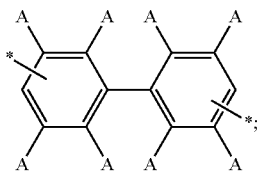

wherein, in the

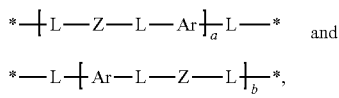 and

*-L-* is a $C_{1-10}$ alkylene group (*—$(CH_2)_c$—*, wherein c is an integer of 1 to 10), a $C_{1-10}$ alkyleneoxy group (*—$(CH_2)_d$—O—*, wherein d is an integer of 1 to 10),

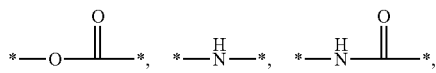

*—CH=CH—*, or *—C≡C—*,

*—Z—* is *—$(CH_2)_e$—* (wherein e is an integer of 0 to 12), and

*—Ar—* is

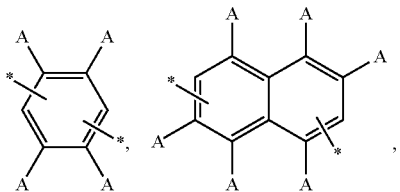

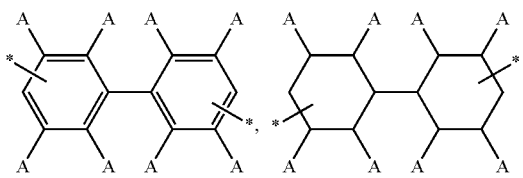

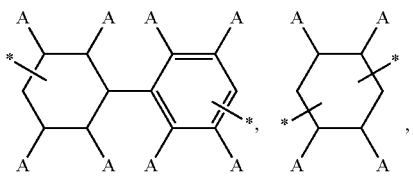

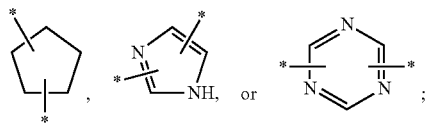

and
wherein, in the

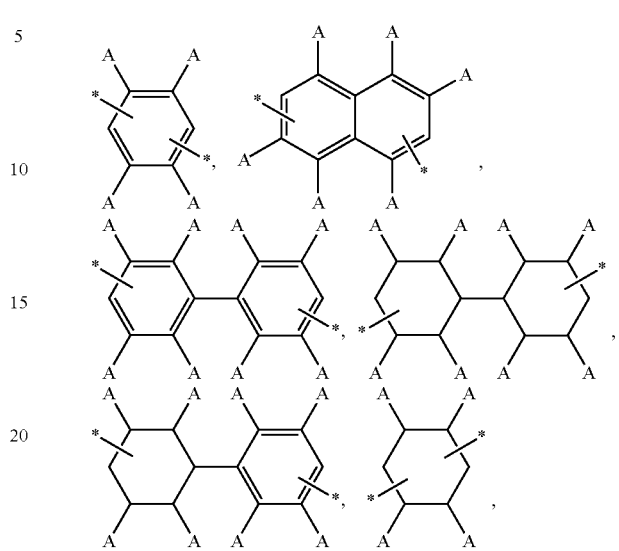

A-* is H—*, a $C_{1-10}$ alkyl group, F—*, Cl—*, Br—*, I—*, *—OH, *—$NH_2$, or CN—*.

According to an exemplary embodiment, there is provided a liquid crystal display device, including:
a display substrate including a first base substrate,
a switching element disposed on the first base substrate, and
a first electrode disposed on the switching element;
a counter display substrate including a second base substrate and a second electrode disposed on the second base substrate and facing the display substrate; and
a liquid crystal layer containing at least one compound represented by Formula 1-A and a reactive mesogen of at least one compound represented by Formula RM, wherein the liquid crystal layer is disposed between the display substrate and the counter display substrate:

Formula 1-A

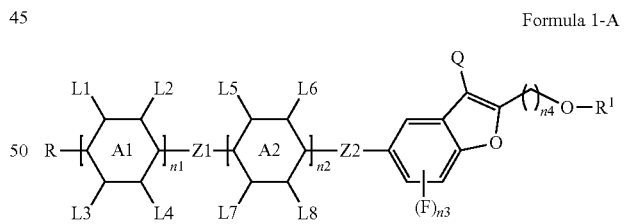

wherein, in the Formula 1-A,
R—* is *—H, *—F, *—Cl, *—Br, *—I, a $C_{1-12}$ alkyl group, or a cyano group, and
$R^1$—* is a $C_{1-12}$ alkyl group;
Q-* is *—H or a $C_{1-5}$ alkyl group;
*—Z1-* and *—Z2-* are the same or different and are each independently *—O—*, *—COO—*, *—OCO—*, *—$CF_2O$—*, *—$OCF_2$—*, *—$CH_2O$—*, *—$OCH_2$—*, *—$SCH_2$—*, *—$CH_2S$—*, *—$C_2F_4$—*, *—$CH_2CF_2$—*, *—$CF_2CH_2$—*, *—$(CH_2)_m$—* (wherein m is an integer of 1 to 5), *—CH=CH—*, *—CF=CF—*, *—CH=CF—*, *—CF=CH—*, *—C≡C—*, *—$CH=CHCH_2O$—*, or a single bond;

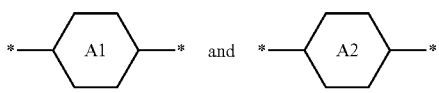

are the same or different and are each independently

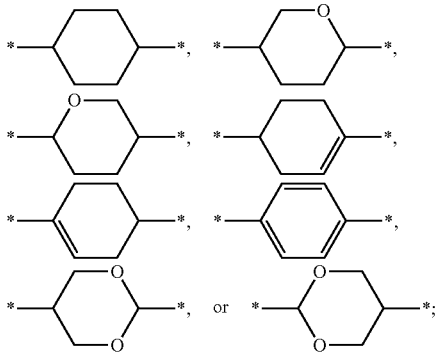

n1 and n2 are each independently an integer of 0 to 3;
n3 is an integer of 1 to 3;
n4 is an integer of 1 or 2; and
L1-*, L2-*, L3-*, L4-*, L5-*, L6-*, L7-*, and L8-* are the same or different and are each independently *—H, *—F, *—Cl, *—OCF$_3$, *—CF$_3$, *—CH$_2$F, or *—CHF$_2$.

P1-SP1-MG-SP2-P2    Formula RM wherein, in the Formula RM,

P1-* and P2-* are the same or different and are each independently

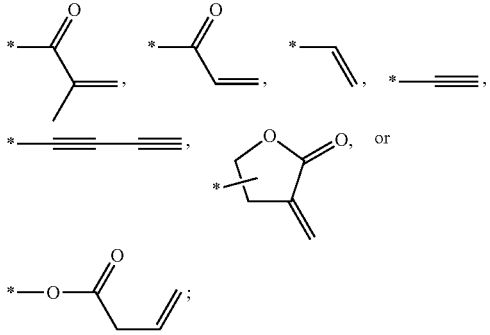

*—SP1-* is

*—(L—Z—L—Ar)$_a$—L—*

(wherein a is an integer of 0 to 2);
*—PS2-* is

*—L—(Ar—L—Z—L)$_b$—*

(wherein b is integer of 0 to 2);

*-MG-* is

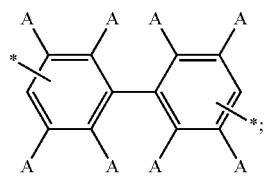

wherein, in the

*—(L—Z—L—Ar)$_a$—L—*  and

*—L—(Ar—L—Z—L)$_b$—*,

*-L-* is a C$_{1-10}$ alkylene group (*—(CH$_2$)$_c$—*, wherein c is an integer of 1 to 10), a C$_{1-10}$ alkyleneoxy group (*—(CH$_2$)$_d$—O—*, wherein d is an integer of 1 to 10),

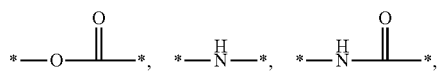

*—CH=CH—*, or *—C≡C—*, *—Z—* is *—(CH$_2$)$_e$—* (wherein e may be an integer of 0 to 12), and *—Ar—* may be

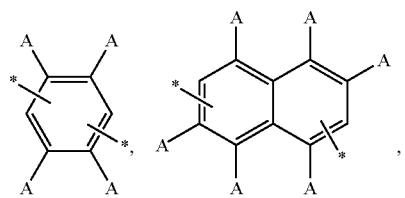

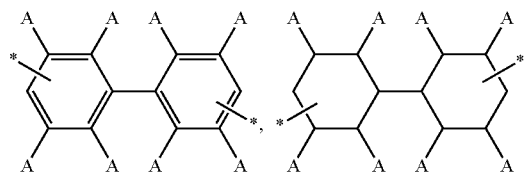

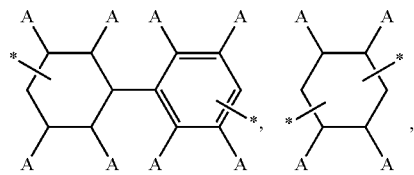

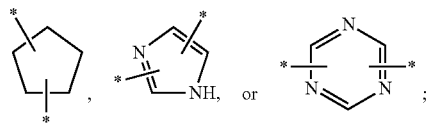

and
In the

[structures with A substituents]

A-* is H—*, alkyl of $C_{1-10}$, F—*, Cl—*, Br—*, I—*, *—OH, *—$NH_2$, or CN—*.

In the Formula 1-A,
Q-* may be *—H, and
n4 may be an integer of 1.
In the Formula 1-A,
Q-* may be *—H, and
n3 may be an integer of 2.
In the Formula 1-A,

[A1 and A2 ring structures]

may be the same or different and may each independently be

[cyclohexyl or phenyl structures]

and
*—Z1-* and *—Z2-* may each be a single bond.

In an exemplary embodiment, the at least one compound represented by Formula 1-A may be a compound represented by Formula 1-B:

Formula 1-B

[Formula 1-B structure with L1-L8, A1, A2, Z1, Z2, R, R¹]

wherein, in the Formula 1-B, A1, A2, L1-*, L2-*, L3-*, L4-*, L5-*, L6-*, L7-*, L8-*, R—*, $R^1$—*, *—Z1-*, *—Z2-*, n1, and n2 are the same as in the Formula 1-A.

In an exemplary embodiment, the liquid crystal display device may further include
a liquid crystal alignment layer including a polymer of the reactive mesogen,
wherein the liquid crystal alignment layer is disposed between the liquid crystal layer and at least one of the display substrate and the counter display substrate.

In an exemplary embodiment, the at least one compound represented by Formula 1-A may be a compound represented by Formulae 1-1 to 1-4:

Formula 1-1

Formula 1-2

Formula 1-3

Formula 1-4

In an exemplary embodiment, the liquid crystal layer may further include at least one compound represented by Formulae 2-1 to 2-17:

Formula 2-1

Formula 2-2

Formula 2-3

Formula 2-4

Formula 2-5

Formula 2-6
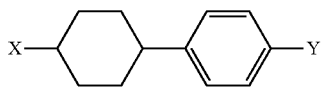

Formula 2-7
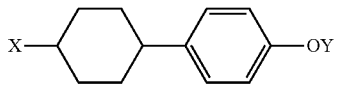

Formula 2-8
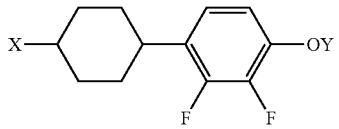

Fromula 2-9
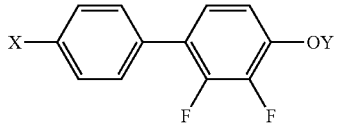

Formula 2-10
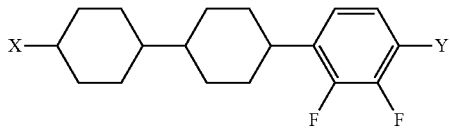

Formula 2-11
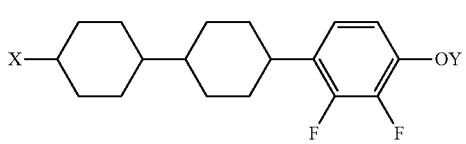

Formula 2-12
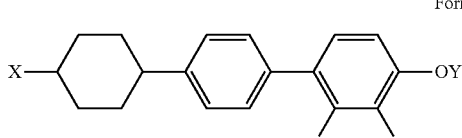

Formula 2-13
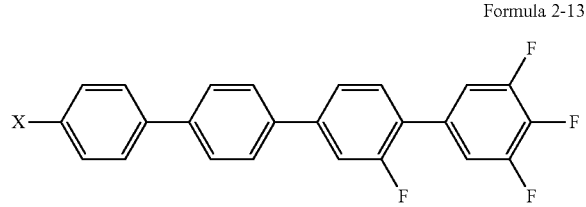

Formula 2-14
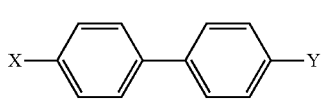

Formula 2-15
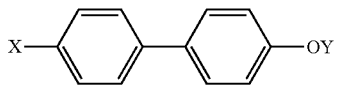

Formula 2-16
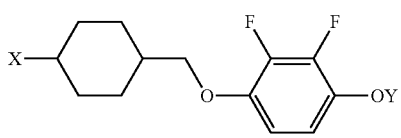

Formula 2-17
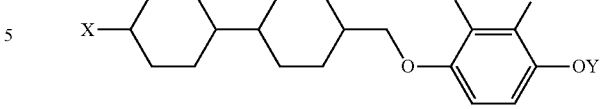

wherein, in the Formulae 2-1 to 2-17,
X—* and Y—* are each independently a $C_{1-5}$ alkyl group.

In an exemplary embodiment, the content of at least one compound represented by Formula P may be 0 percent by weight:

Formula P
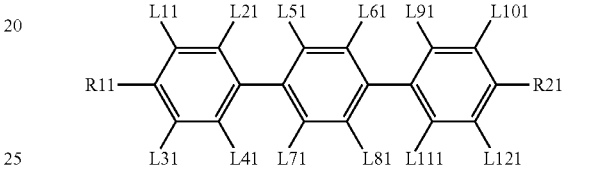

wherein, in the Formula P,
L11-*, L21-*, L31-*, L41-*, L51-*, L61-*, L71-*, L81-*, L91-*, L101-*, L111-*, and L121-* are the same or different and are each independently H—* or F—*; and
R11-* and R12-* are the same or different and are each independently a $C_{1-5}$ alkyl group or a $C_{1-5}$ alkoxy group.

In an exemplary embodiment, the content of the at least one compound represented by Formula 1-A is about 1 percent by weight to about 10 percent by weight based on the total weight of the liquid crystal layer.

As described below, according to the present disclosure, there is provided a low-viscosity liquid crystal composition having high reliability and a liquid crystal display device including the same.

BRIEF DESCRIPTION OF THE DRAWINGS

The above and other aspects and features of the present disclosure will become more apparent by describing in detail exemplary embodiments thereof with reference to the attached drawings, in which.

DETAILED DESCRIPTION

Figure 1:
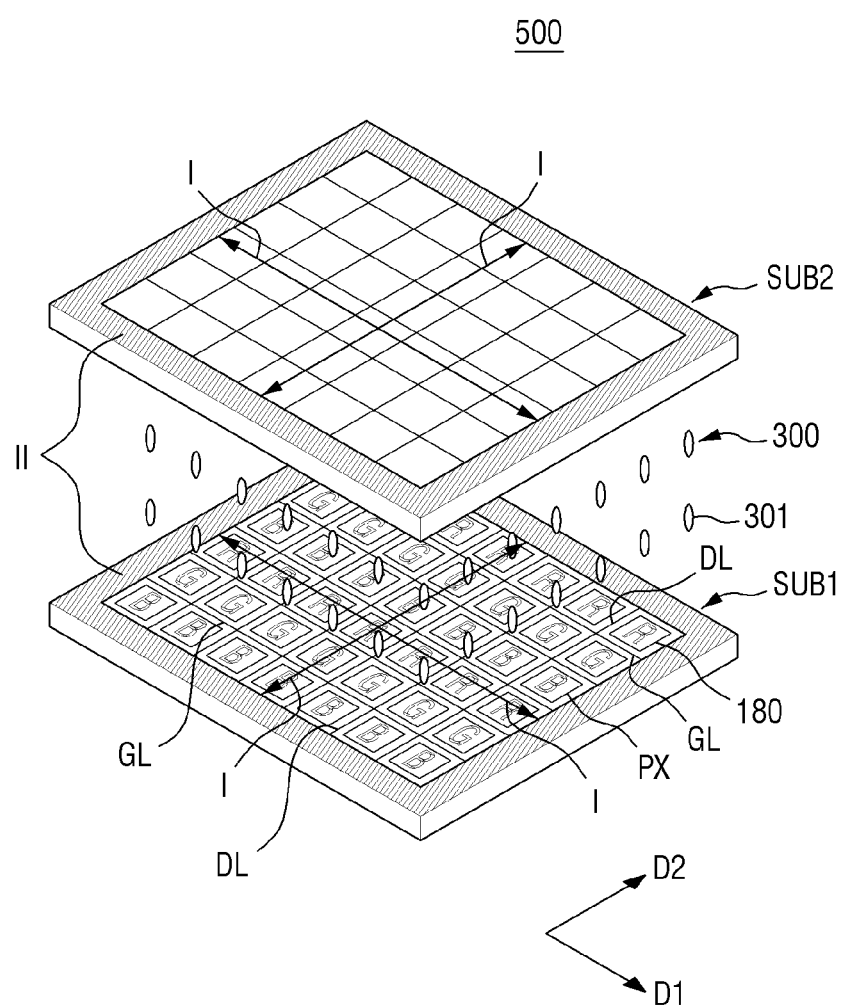
FIG. 1 is a schematic exploded perspective view of a first liquid crystal display device.

Features of the inventive concept and methods of accomplishing the same may be understood more readily by reference to the following detailed description of embodiments and the accompanying drawings.

The inventive concept may, however, be embodied in many different forms and should not be construed as being limited to the embodiments set forth herein. Rather, these embodiments are provided so that this disclosure will be thorough and complete and will fully convey the concept of the inventive concept to those skilled in the art, and the inventive concept will only be defined by the appended claims.

In the drawings, the thickness of layers and regions are exaggerated for clarity. It will be understood that when an element or layer is referred to as being "on," "connected to" or "coupled to" another element or layer, the element or layer can be directly on, connected or coupled to another element or layer or intervening elements or layers. In contrast, when an element is referred to as being "directly on," "directly connected to" or "directly coupled to" another element or layer, there are no intervening elements or layers present. As used herein, connected may refer to elements being physically, electrically and/or fluidly connected to each other.

Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the disclosure.

Spatially relative terms, such as "bottom," "below," "lower," "under," "above," "upper," "top" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features.

Moreover, sharp angles that are illustrated may be rounded. Thus, the regions illustrated in the figures are schematic in nature and their shapes are not intended to illustrate the precise shape of a region and are not intended to limit the scope of the present claims.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "alkoxy group" refers to "alkyl-O—", wherein the term "alkyl" has the same meaning as described above.

As used herein, when a definition is not otherwise provided, the term "alkylene group" refers to a straight or branched saturated aliphatic hydrocarbon group having a valence of at least two, optionally substituted with one or more substituents.

As used herein, when a definition is not otherwise provided, the term "alkyleneoxy group" refers to "alkylene-O—" or "—O-alkylene", wherein the term "alkylene" has the same meaning as described above.

In the present specification, the "$C_{A\text{-}B}$" means that the number of carbon atoms is equal to or more than A and equal to or less than B. In the present specification, the "A to B" is defined as equal to or more than A and equal to or less than B. In the present specification, the symbol "*" is defined as a bonding site in which adjacent elements are covalently bonded to each other. For example, an ethoxy group is a monovalent atomic group in which each of a methyl group ($CH_3$—*) and an ether group (*—O—*) is bonded to methylene (*—CH$_2$—*) and is represented by CH$_3$—CH$_2$—O—*, and ethyl methyl ether is a compound in which each of an ethyl group (CH$_3$—CH$_2$—*) and a methyl group (CH$_3$—*) is bonded to an ether group (*—O—*) and is represented by CH$_3$—CH$_2$—O—CH$_3$.

Figure 2:
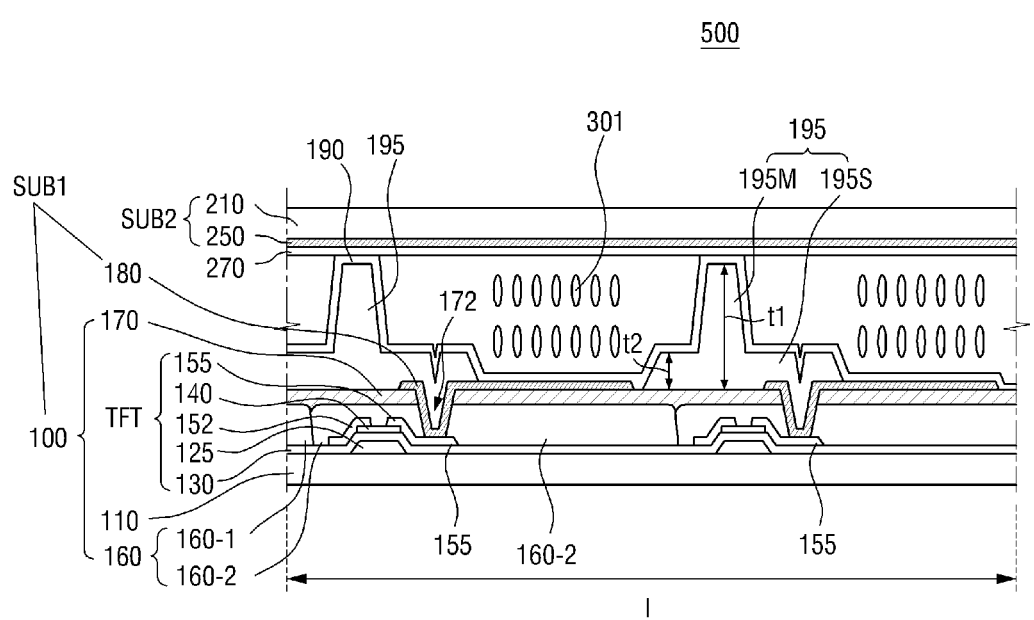
FIG. 2 is a schematic cross-sectional view of the initial state of the first liquid crystal display device of FIG. 1, to which an electric field is not applied.

FIG. 1 is a schematic exploded perspective view of a liquid crystal display device 500 including a display substrate SUB1 and a counter display substrate SUB2, and FIG. 2 is a schematic partial cross-sectional view of the display area I of the liquid crystal display device 500 of FIG. 1.

Referring to FIG. 1, the liquid crystal display device 500 may be configured to include: a display substrate SUB1; a counter display substrate SUB2 disposed to face the display substrate SUB1, and may be spaced apart from the display substrate SUB1 while maintaining a predetermined distance; and a liquid crystal layer 300 disposed between the display substrate SUB1 and the counter display substrate SUB2. The liquid crystal layer 300 may include liquid crystal compound molecules 301, and the liquid crystal compound molecules 301 may have negative dielectric anisotropy.

The liquid crystal display device 500 includes a display area I and a non-display area II. The display area I is an area in which an image is displayed. The non-display area II is a peripheral area surrounding the display area I, and is an area in which an image is not displayed.

The display substrate SUB1 may include a plurality of gate lines GL extending in a first direction and a plurality of data line DL extending in a second direction perpendicular to the first direction. Although not shown in the drawings, the gate lines GL are not disposed only in the display area I, and may extend to the non-display area II. In this case, the non-display area II may be provided with a gate pad (not shown). That is, in the non-display area II, the display substrate SUB1 may include a gate pad (not shown). Further, the data lines DL are not disposed only in the display area I, and may extend to the non-display area II. In this case, the non-display area II may be provided with a data pad (not shown). That is, in the non-display area II, the display substrate SUB1 may include a data pad (not shown).

A plurality of pixels PX defined by the gate lines GL the data lines DL may be disposed in the display area I. The plurality of pixels PX may be arranged in the form of a matrix, and a first electrode 180 may be disposed for each of the pixels PX. In this case, in the display area I, the display substrate SUB1 may include the plurality of pixels PX arranged in the form of a matrix and the plurality of first electrodes 180 arranged in the form of a matrix.

In the non-display area II, a drive unit (not shown) for providing a gate drive signal and a data drive signal to each of the pixels PX may be disposed. In this case, in the non-display area II, the display substrate SUB1 may include a drive unit (not shown). The drive unit (not shown) may generate a gate drive signal and a data drive signal corresponding to a drive frequency of 120 Hertz (Hz) or more.

The display substrate SUB1 may include a switching element array substrate (not shown) and a first electrode (not shown), and the counter display substrate SUB2 may include a second base substrate (not shown) and a second electrode (not shown). Hereinafter, the display substrate SUB1, the counter display substrate SUB2, and the liquid crystal layer 300 will be described in more detail with reference to FIGS. 1 and 2.

Referring to FIGS. 1 and 2, the display substrate SUB1 may be configured to include a switching element array substrate 100 and a first electrode 180. The switching element array substrate 100 may be configured to include a first base substrate 110, a switching element TFT disposed on the first base substrate 110, a color filter layer 160 disposed on the switching element TFT, and an organic film 170 disposed on the color filter layer 160.

The counter display substrate SUB2, which is a counter substrate of the display substrate SUB1, may be configured to include a second base substrate 210 and a second electrode 250.

The liquid crystal display device 500 may further include a light-blocking spacer 195, a first liquid crystal alignment layer 190, and a second liquid crystal alignment layer 270. The light-blocking spacer 195 may be disposed between the first electrode 180 and the second electrode 250, and may include an area overlapping the switching element TFT. The light-blocking spacer 195 serves as both a spacer for maintaining the thickness of the liquid crystal layer 300 and a black matrix. The first liquid crystal alignment layer 190 may be disposed on the display substrate SUB1, and may include an area disposed between the first electrode 180 and the liquid crystal layer 300. The second liquid crystal alignment layer 270 may include an area disposed between the second electrode 250 and the liquid crystal layer 300. Further, the first liquid crystal alignment layer 190 may include an area disposed between the light-blocking spacer 195 and the second liquid crystal alignment layer 270, and the second liquid crystal alignment layer 270 may include an area disposed between the first liquid crystal alignment layer 190 and the second electrode 250.

The liquid crystal display device 500 is realized by a polymer stabilized-vertical alignment mode (PS-VA mode). The PS-VA mode, which is a technology for stabilizing the pretilt alignment of liquid crystal compound molecules 301 through a polymer network composed of polymers of reactive mesogens, may be performed by a first method and a second method to be described in detail later.

In the first method, vertical alignment films not containing the reactive mesogens (hereinafter, referred to as "N vertical alignment films") face each other, the liquid crystal composition containing the reactive mesogens is disposed between the N vertical alignment films to form a liquid crystal cell, and then the liquid crystal cell is exposed to ultraviolet rays in an electric field, thereby forming the polymer network on the N vertical alignment films.

In the second method, vertical alignment films containing the reactive mesogens (hereinafter, referred to as "RM vertical alignment films") are formed on at least one electric field generating electrode of the first electrode 180 and the second electrode 250 using the liquid crystal aligning agent containing the reactive mesogens, the liquid crystal composition is disposed between the RM vertical alignment films to form a liquid crystal cell, and then the liquid crystal cell is heat-treated to elute the reactive mesogens from the RM vertical alignment films to the liquid crystal composition, and then the heat-treated liquid crystal cell is exposed to ultraviolet rays, thereby forming the polymer network on the RM vertical alignment films. In this case, the reactive mesogens may be added to the liquid crystal composition, and may not be added thereto.

The reactive mesogen is a compound having a mesogenic structure for expressing liquid crystallinity and a polymerizable end group for polymerization. For example, the reactive mesogen may be represented by Formula RM below.

P1-SP1-MG-SP2-P2　　　　　　　　　　Formula RM

In the Formula RM, P1-* and P2-* may be each independently

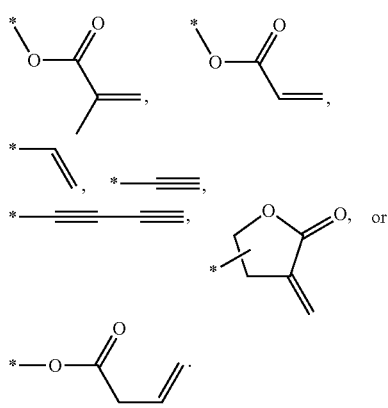

and P2-* may be the same as or different from each other.

In the Formula RM, *—SP1-* may be

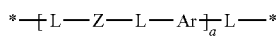

(wherein a may be an integer of 0 to 2), *—SP2-* may be

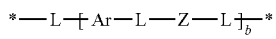

(wherein b may be an integer of 0 to 2), and *-MG-* may be

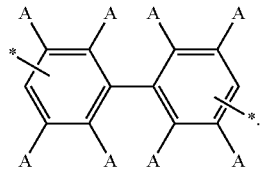

In the

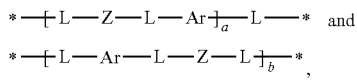

*-L-* may be a single bond, a $C_{1-10}$ alkylene group (*—$(CH_2)_c$—*, wherein c is an integer of 1 to 10), a $C_{1-10}$ alkyleneoxy group (*—$(CH_2)_d$—O—*, wherein d is an integer of 1 to 10),

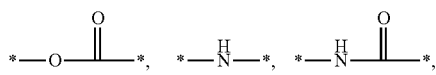

*—CH=CH—*, or *—C≡C—*; and *—Z—* may be *—$(CH_2)_e$—* (wherein e may be an integer of 0 to 12).

In the

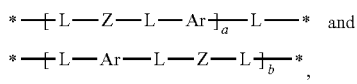

*—Ar—* may be

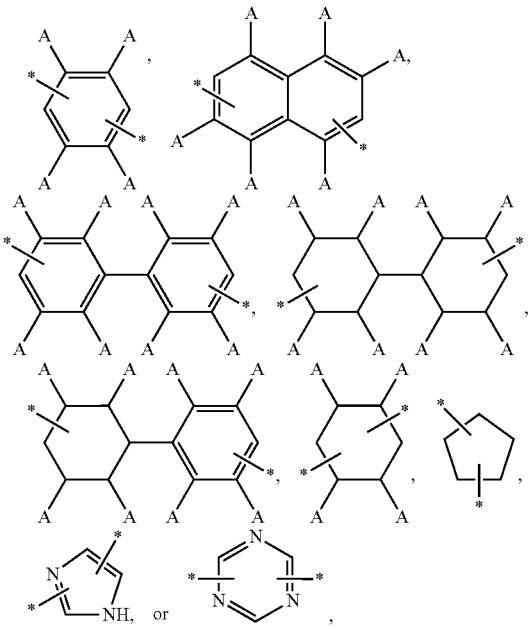

In the

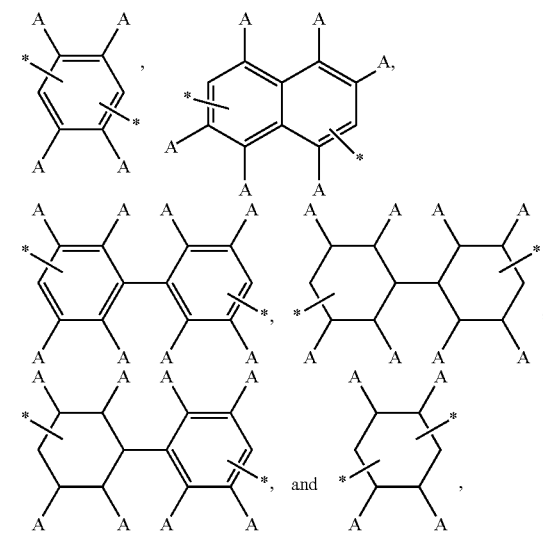

A-* may be H—*, a $C_{1-10}$ alkyl group, F—*, Cl—*, Br—*, I—*, *—OH, *—$NH_2$, or CN—*.

The reactive mesogen, for example, may be at least one compound represented by Formula RM1 below.

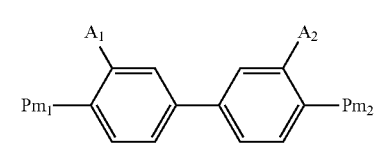

Formula RM1

In the Formula RM1, $Pm_1$—* and $Pm_2$—* may be each independently

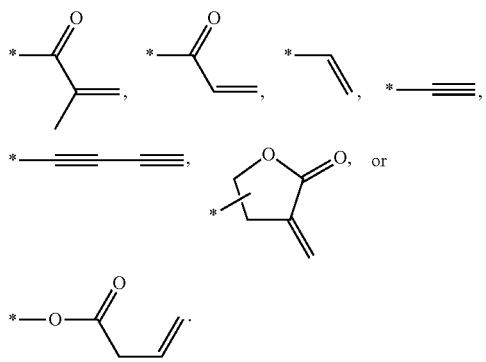

Pm₁—* and Pm₂—* may be the same as or different from each other.

In the Formula RM1, each of $A_1$-* and $A_2$-* may be *—H, *—F, *—Cl, Br—*, *—I, *—OH, *—NH₂, or *—CN. $A_1$-* and $A_2$-* may be the same as or different from each other.

Meanwhile, both the first method and the second method require an ultraviolet exposure process for polymerizing the reactive mesogens. Therefore, it is preferred that the liquid crystal layer 300 is composed of the liquid crystal compound molecules 301 having excellent photo stability.

The ultraviolet exposure process may be performed using ultraviolet rays having a wavelength of about 300 nanometers (nm) or more. A compound represented by Formula P below absorbs ultraviolet rays having a wavelength of about 260 nm to 380 nm. Therefore, the compound represented by Formula P below has poor stability to ultraviolet rays having a wavelength of about 260 nm to 380 nm. When the liquid crystal layer 300 contains the compound represented by Formula P below, the voltage holding rate (VHR) is lowered, and line afterimage and stains are generated, thereby deteriorating the reliability of the first liquid crystal display device 500. Therefore, it is preferable that the liquid crystal layer 300 does not contain the compound represented by Formula P.

Formula P

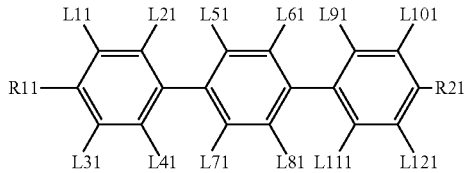

In the Formula P, L11-*, L21-*, L31-*, L41-*, L51-*, L61-*, L71-*, L81-*, L91-*, L101-*, L111-*, and L121-* may be each independently H—* or F—*, and L11-*, L21-*, L31-*, L41-*, L51-*, L61-*, L71-*, L81-*, L91-*, L101-*, L111-*, and L121-* may be the same as or different from each other. In the Formula P, R11-* and R12-* may be each independently a $C_{1-5}$ alkyl group or a $C_{1-5}$ alkoxy group, and R11-* and R12-* may be the same as or different from each other.

For example, the compound represented by Formula P above may be at least one compound represented by Formulae P-1 and P-2 below.

Formula P-1

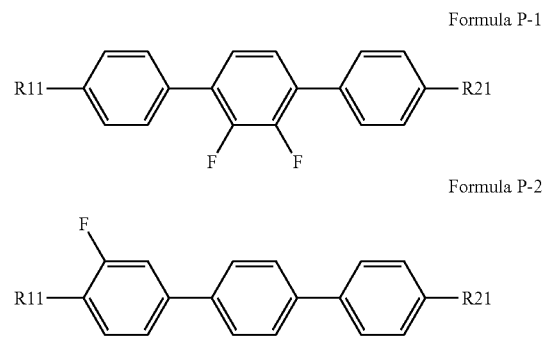

Formula P-2

As described above, the counter display substrate SUB2 is a counter substrate of the display substrate SUB1, which includes the second base substrate 210 and the second electrode 250. In this case, the second electrode 250 may be directly disposed on the second base substrate 210. The first liquid crystal display device 500 may be configured such that the display substrate SUB1 includes the color filter layer 160 and the light-blocking spacer 195, and the counter display substrate SUB2 does not include a color filter and a black matrix. In this case, at the time of the ultraviolet exposure process, the exposure amount of ultraviolet light incident on the liquid crystal layer 300 increases, compared to the embodiment where the counter display substrate SUB2 is designed to have a structure including a color filter and a black matrix. Therefore, the first liquid crystal display device 500 particularly has a problem of reliability deterioration due to the compound represented by Formula P above. Accordingly, it is preferable that the content of the compound represented by Formula P above in the liquid crystal layer 300 is 0 percent by weight.

Meanwhile, in the polymer stabilized-vertical alignment mode, the compound represented by Formula P above serves to promote the polymerization reaction of the reactive mesogens. Therefore, in order to realize the first liquid crystal display device 500 in the polymer stabilized-vertical alignment mode, a novel liquid crystal compound capable of promoting the polymerization reaction of the reactive mesogens is desired instead of the compound represented by Formula P above.

The liquid crystal layer 300 may contain a compound represented by Formula 1-A below instead of the compound represented by Formula P above.

Formula 1-A

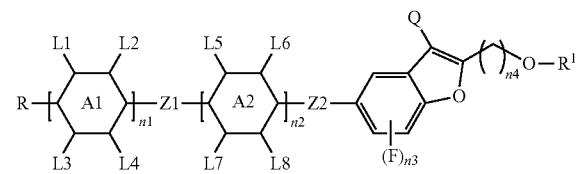

In the Formula 1-A, R—* is *—H, *—F, *—Cl, *—Br, *—I, a $C_{1-12}$ alkyl group, or a cyano group, and $R^1$—* is a $C_{1-12}$ alkyl group. In the Formula 1-A, Q-* is *—H or a $C_{1-5}$ alkyl group. In the Formula 1-A, *—Z1-* and *—Z2-* are each independently *—O—*, *—COO—*, *—OCO—*, —CF₂O—*, —OCF₂—*, *—CH₂O—*, *—OCH₂—*, *—SCH₂—*, *—CH₂S—*, *—C₂F₄—*, *—CH₂CF₂—*, *—CF₂CH₂—*, *—(CH₂)ₘ—* (wherein m is an integer of 1 to 5), *—CH=CH—*, *—CF=CF—*, *—CH=CF—*, *—CF=CH—*, *—C≡C—*, *—CH=CHCH₂O—*, or a single bond. *—Z1-* and *—Z2-* may be the same as or different from each other.

In the Formula 1-A, are each

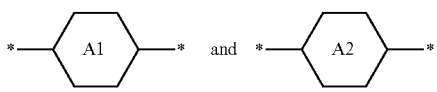

are each independently

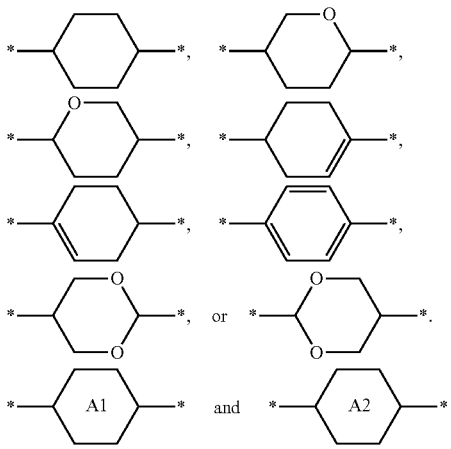

may be the same as or different from each other.

In the Formula 1-A, n1 and n2 are each independently an integer of 0 to 3, n3 is an integer of 1 to 3, n4 is an integer of 1 or 2, and L1-*, L2-*, L3-*, L4-*, L5-*, L6-*, L7-*, and L8-* are each independently *—H, *—F, *—Cl, *—OCF₃, *—CF₃, *—CH₂F, and *—CHF₂. L1-*, L2-*, L3-*, L4-*, L5-*, L6-*, L7-*, and L8-* may be the same as or different from each other.

In the Formula 1-A, Q-* may be *—H and n4 may be an integer of 1. In the Formula 1-A, Q-* may be *—H, and n3 may be an integer of 2.

In the Formula 1-A,

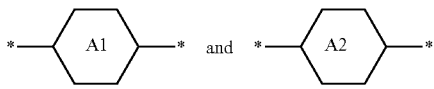

may be the same or different and may each independently be

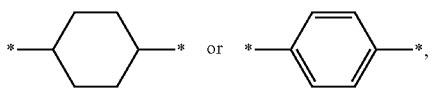

and *—Z1-* and *—Z2-* may each be a single bond.

In an exemplary embodiment, the at least one compound represented by Formula 1-A may be a compound represented by Formula 1-B:

Formula 1-B

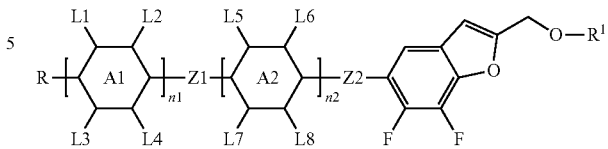

wherein, in the Formula 1-B, A1, A2, L1-*, L2-*, L3-*, L4-*, L5-*, L6-*, L7-*, L8-*, R—*, R¹—*, *—Z1-*, *—Z2-*, n1, and n2 are the same as in the Formula 1-A.

The compound represented by Formula 1-A above has a benzofuran alkyl ether structure. Due to the benzofuran alkyl ether structure, the compound represented by Formula 1-A above has high refractive index characteristics, high electric constant characteristics, and high phase transition temperature (Tni), compared to a comparative compound not having the benzofuran alkyl ether structure. Therefore, when the comparative compound is replaced by the compound represented by Formula 1-A above, a liquid crystal composition having a high refractive index, a dielectric constant, and a high phase transition temperature can be prepared.

Further, when the compound represented by Formula P above is replaced by the compound represented by Formula 1-A above, the compound represented by Formula 1-A above can promote the polymerization reaction of the reactive mesogens, and thus black afterimages of the first liquid crystal display device 500 can be improved. That is, the compound represented by Formula 1-A above can improve the reliability of the first liquid crystal display device 500.

The liquid crystal layer 300 may contain the compound represented by Formula 1-A above in an amount of about 1 wt % to about 10 wt % based on the total weight of the liquid crystal composition. When the content of the compound represented by Formula 1-A above is more than about 10 wt %, high-temperature stability may be deteriorated due to crystallization.

The compound represented by the Formula 1-A above, for example, may be a compound represented by Formulae 1-1 to 1-4 below.

Formula 1-1

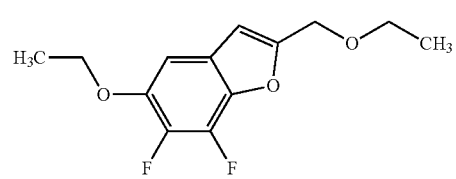 [SMILES: CCOCc1cc2cc(OCC)c(F)c(F)c2o1]

Formula 1-2

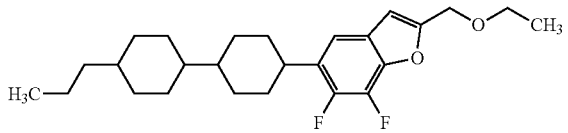

Formula 1-3

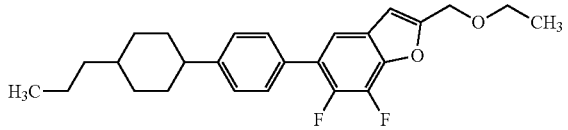

-continued

Formula 1-4

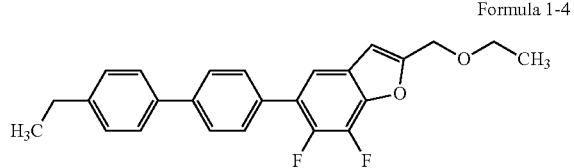

The simulation results of the phase transition temperature (Tni), refractive index anisotropy (Δn), dielectric anisotropy (Δε) and rotational viscosity (γ1) of the compounds (BF1, BF2, BF3, and BF4) represented by the Formulae 1-1 to 1-4 are summarized in Table 1 below. The simulation results of the phase transition temperature (Tni), refractive index anisotropy (Δn), dielectric anisotropy (Δε) and rotational viscosity (γ1) of the comparative compounds (CC1, CC2, CC3, CC4, CC5, and CC6) are summarized in Table 2 below.

TABLE 1

| Liquid Crystal Compound | Structural Formula | Tni (° C.) | Δε (ε∥ − ε⊥) | Δn (ne − no) | γ1 (mPa · s) |
|---|---|---|---|---|---|
| BF1 | | 89 | −9.20 | 0.178 | 270 |
| BF2 | | 153.4 | −13.22 | 0.179 | 780 |
| BF3 | | 172.3 | −12.74 | 0.245 | 774 |
| BF4 | | 132.7 | −10.70 | 0.317 | 612 |

TABLE 2

| Liquid Crystal Compound | Structural Formula | Tni (° C.) | Δε (ε∥ − ε⊥) | Δn (ne − no) | γ1 (mPa · s) |
|---|---|---|---|---|---|
| CC1 | | 60.4 | −4.94 | 0.106 | 72 |
| CC2 | | 50.2 | −5.12 | 0.157 | 70 |

TABLE 2-continued

| Liquid Crystal Compound | Structural Formula | Tni (° C.) | Δε (ε∥ -ε⊥) | Δn (ne - no) | γ1 (mPa·s) |
|---|---|---|---|---|---|
| CC3 | H₃C—O—⌬(F,F)—O—CH₃ | 23.5 | -5.15 | 0.000 | 12 |
| CC4 | H₃C—⌬—⌬—⌬(F,F)—O—CH₃ | 101.1 | -6.12 | 0.083 | 474 |
| CC5 | H₃C—⌬—⌬—⌬(F,F)—O—CH₃ | 107.4 | -6.05 | 0.158 | 464 |
| CC6 | H₃C—⌬—⌬(F,F)—⌬—CH₃ | 93.9 | -3.10 | 0.244 | 276 |

The results of measurement of the phase transition temperature (Tni), refractive index anisotropy (Δn), dielectric anisotropy (Δε), elastic modulus (K33) and rotational viscosity (γ1) of the liquid crystal compositions of Comparative Examples (hereinafter, referred to as "comparative liquid crystal compositions") not containing the compounds (BF1, BF2, BF3, and BF4) represented by the Formulae 1-1 to 1-4 are summarized in Table 3 below.

The results of measurement of the phase transition temperature (Tni), refractive index anisotropy (Δn), dielectric anisotropy (Δε), elastic modulus (K33) and rotational viscosity (γ1) of the liquid crystal compositions of Examples (hereinafter, referred to as "first liquid crystal compositions") containing the compounds (BF1 and BF4) represented by the Formulae 1-1 and 1-4 are summarized in Table 4 below.

The results of measurement of the phase transition temperature (Tni), refractive index anisotropy (Δn), dielectric anisotropy (Δε), elastic modulus (K33) and rotational viscosity (γ1) of the liquid crystal compositions of Examples (hereinafter, referred to as "second liquid crystal compositions") containing the compounds (BF1 and BF3) represented by the Formulae 1-1 and 1-3 are summarized in Table 5 below.

The results of measurement of the phase transition temperature (Tni), refractive index anisotropy (Δn), dielectric anisotropy (Δε), elastic modulus (K33) and rotational viscosity (γ1) of the liquid crystal compositions of Examples (hereinafter, referred to as "third liquid crystal compositions") containing the compounds (BF1, BF2, BF3, and BF4) represented by the Formulae 1-1 to 1-4 are summarized in Table 6 below.

In Tables 3 to 6,

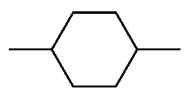

is named as "C",

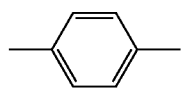

is named as "P",

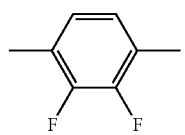

is named as "A",

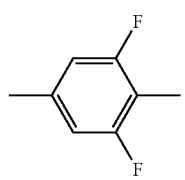

is named as "K",

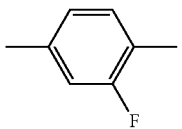

is named as "L",

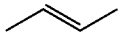

is named as "V",

and is named as "V1".

For example,

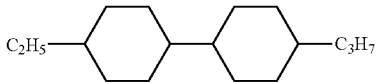

may be named as "2CC3",

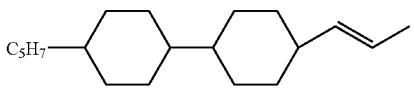

may be names as "3CCV",

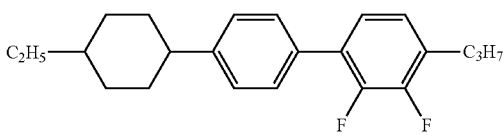

may be names as "2CPA3",

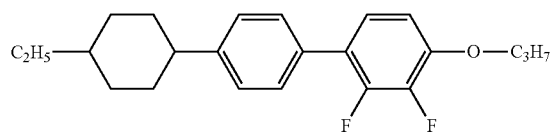

may be named as "2CPAO3", and

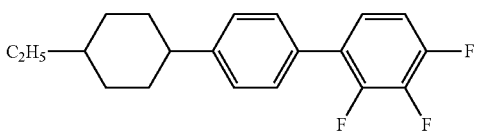 [SMILES: CCC1CCC(c2ccc(-c3ccc(F)c(F)c3F)cc2)CC1]

may be named as "2CPAF".

TABLE 3

| Comparative Example | Liquid crystal compound | Content (wt %) | Physical properties |
|---|---|---|---|
| 1 | 2CC3 | 22 | Tni(° C.): 75.5 |
| 2 | 3CCV4 | 9 | Δn (ne − no): 0.108 |
| 3 | 3CPO1 | 7 | Δε (ε // − ε⊥): −3.0 |
| 4 | 3CAO2 | 15 | K33: 13.0 |
| 5 | 4CCAO2 | 9.5 | γ1 (mPa · s): 120 |
| 6 | 5CCAO2 | 5 | |
| 7 | 2CPAO2 | 9 | |
| 8 | 3CPAO2 | 9 | |
| 9 | 2PAP3 | 7 | |
| 10 | 3PAP4 | 7.5 | |

TABLE 4

| Example | Liquid crystal compound | Content (wt %) | Physical properties |
|---|---|---|---|
| 1 | 3CCV | 10 | Tni(° C.): 76.5 |
| 2 | 3CCV1 | 15 | Δn(ne − no): 0.108 |
| 3 | VCCP1 | 5 | Δε(ε // − ε⊥): −3.0 |
| 4 | 2CC3 | 10 | K33: 13.2 |
| 5 | BF1 | 7 | γ1 (mPa · s): 95 |
| 6 | BF4 | 5 | |
| 7 | 3CCP1 | 5 | |
| 8 | 3CAO2 | 11 | |
| 9 | 3PAO2 | 15 | |
| 10 | 3CCAO2 | 8 | |
| 11 | 2CCA1 | 5 | |
| 12 | 2CPAO2 | 4 | |

Referring to Tables 3 and 4 above, each of the first liquid crystal compositions could ensure low-viscosity characteristics compared to the comparative liquid crystal compositions by replacing terphenyl liquid crystal compounds, such as 2PAP3 and 3PAP4, having poor stability to ultraviolet rays of about 260 nm to 380 nm with BF1 and BF4. Therefore, each of the first liquid crystal compositions can provide high-speed response characteristics to the first liquid crystal display device 500.

TABLE 5

| Example | Liquid crystal compound | Content (wt %) | Physical properties |
|---|---|---|---|
| 1 | 3CCV | 15 | Tni(° C.): 74.5 |
| 2 | 3CCV1 | 10 | Δn(ne − no): 0.108 |
| 3 | 2CC3 | 10 | Δε(ε // − ε⊥): −3.6 |
| 4 | BF1 | 5 | K33: 14.0 |
| 5 | BF3 | 5 | γ1 (mPa · s): 115 |
| 6 | 3CCP1 | 3 | |
| 7 | 3CAO2 | 13 | |
| 8 | 3PAO2 | 10 | |
| 9 | 3CCAO2 | 8 | |
| 10 | 2CCA1 | 5 | |
| 11 | 2CPAO2 | 8 | |
| 12 | 3CPAO2 | 8 | |

Referring to Tables 3 and 5 above, each of the second liquid crystal compositions could ensure high dielectric constant characteristics compared to the comparative liquid crystal compositions by replacing terphenyl liquid crystal compounds, such as 2PAP3 and 3PAP4, having poor stability to ultraviolet rays of about 260 nm to 380 nm with BF1 and BF3. Therefore, each of the second liquid crystal compositions can provide high-transmittance characteristics and low-voltage characteristics to the first liquid crystal display device 500.

TABLE 6

| Example | Liquid crystal compound | Content (wt %) | Physical properties |
|---|---|---|---|
| 1 | 3CCV | 15 | Tni(° C.): 100.0 |
| 2 | 3CCV1 | 7 | Δn(ne − no): 0.109 |
| 3 | 2CC3 | 7 | Δε(ε // − ε⊥): −3.5 |
| 4 | 3CC4 | 10 | K33: 17.7 |
| 5 | BF1 | 5 | γ1 (mPa · s): 140 |
| 6 | BF2 | 3 | |
| 7 | BF3 | 3 | |
| 8 | BF4 | 3 | |
| 9 | 3CPO1 | 5 | |
| 10 | 3CCP1 | 7 | |
| 11 | 3CAO4 | 4 | |
| 12 | 3CCAO2 | 15 | |
| 13 | 2CPAO2 | 8 | |
| 14 | 3CPAO2 | 8 | |

Referring to Tables 3 and 6 above, each of the third liquid crystal compositions could ensure high phase transition temperature and high dielectric constant characteristics compared to the comparative liquid crystal compositions by replacing terphenyl liquid crystal compounds, such as 2PAP3 and 3PAP4, having poor stability to ultraviolet rays of about 260 nm to 380 nm with BF1, BF2, BF3, and BF4.

Figure 3:
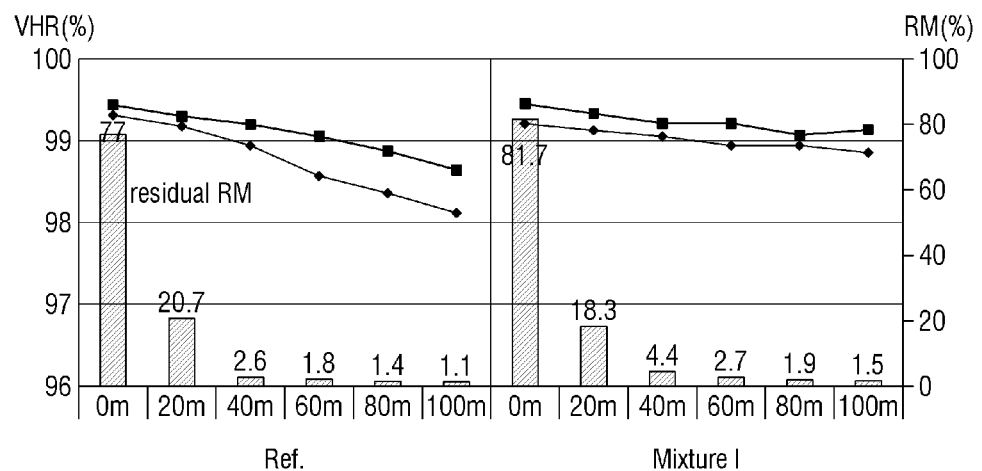
FIG. 3 is a diagram comparing the voltage holding rates and residual reactive mesogen contents according to fluorescence reaction of the liquid crystal compositions of Examples with those of the liquid crystal composition of Comparative Examples.

Meanwhile, FIG. 3 shows a graph comparing the measurement results of the voltage holding rates and residual reactive mesogen contents according to fluorescence reaction of the first liquid crystal composition (Mixture 1) with those of the comparative liquid crystal composition (Ref.). The measurement results of the voltage holding rates are summarized in Table 7 below, and the measurement results of the residual reactive mesogen contents are summarized in Table 8 below. The voltage holding rates thereof were measured under the following conditions.

Frame frequency: 60 Hz (16.64 milliseconds, ms)
Pulse width: 64 microseconds (μs)
Data voltage: 1 volts (V)
Cell gap: 3.0 micrometers (μm) 39
Exposure condition: 6 joules (J), 70 seconds (sec)

TABLE 7

| | Voltage holding rate (%) | | | |
|---|---|---|---|---|
| | Comparative liquid crystal composition (Ref.) | | First liquid crystal composition (Mixture 1) | |
| Time | Initial (0 hr) | After 168 hr (168 hr) | Initial (0 hr) | After 168 hr (168 hr) |
| 0 min | 99.32 | 99.44 | 99.21 | 99.45 |
| 20 min | 99.18 | 99.29 | 99.13 | 99.34 |
| 40 min | 98.94 | 99.19 | 99.06 | 99.21 |
| 60 min | 98.56 | 99.05 | 98.94 | 99.21 |
| 80 min | 98.35 | 98.87 | 98.95 | 99.07 |
| 100 min | 98.12 | 98.63 | 98.85 | 99.14 |

TABLE 8

| | Residual reactive mesogen content according to fluorescence reaction (%) | |
|---|---|---|
| Time | Comparative liquid crystal composition (Ref.) | First liquid crystal composition (Mixture 1) |
| 0 min | 77..0 | 81.7 |
| 20 min | 20.7 | 18.3 |
| 40 min | 2.6 | 4.4 |

TABLE 8-continued

| | Residual reactive mesogen content according to fluorescence reaction (%) | |
|---|---|---|
| Time | Comparative liquid crystal composition (Ref.) | First liquid crystal composition (Mixture 1) |
| 60 min | 1.8 | 2.7 |
| 80 min | 1.4 | 1.9 |
| 100 min | 1.1 | 1.5 |

Referring to Tables 7 and 8 and FIG. 3, the first liquid crystal composition increases a voltage holding rate, and promotes the polymerization reaction of the reactive mesogens, so as to pretilt the liquid crystal compound molecules 301, by replacing terphenyl liquid crystal compounds, such as 2PAP3 and 3PAP4, having poor stability to ultraviolet rays of about 260 nm to 380 nm with BF1 and BF4.

Figure 4:
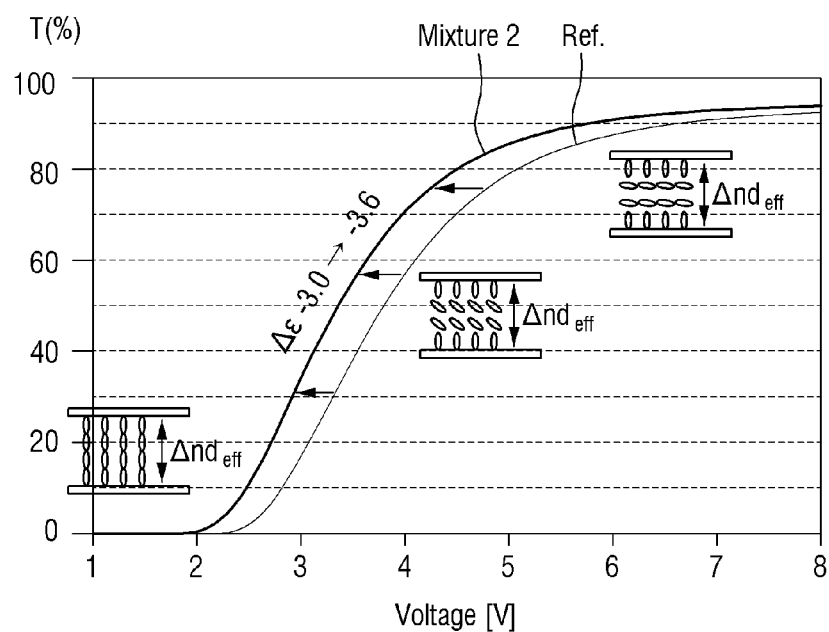
FIG. 4 is a graph of light transmittance (percent, %) versus voltage (volts, V) comparing the measurement results of light transmittance of the liquid crystal cells containing the liquid crystal compositions of Examples with those of the liquid crystal cell containing the liquid crystal composition of Comparative Examples.

FIG. 4 show a graph comparing the measurement results of light transmittance of the liquid crystal cell (Mixture 2) containing the second liquid crystal composition with those of the liquid crystal cell (Ref.) containing the comparative liquid crystal composition. Referring to FIG. 4, the liquid crystal cell (Ref) containing the comparative liquid crystal composition could exhibit high-transmittance characteristics by 8% or more compared to the liquid crystal cell (Mixture 2) containing the second liquid crystal composition.

Referring to FIGS. 1 and 2 again, the first base substrate 110 is a base substrate of the switching element array substrate 100, and may be made of a transparent insulating material, such as glass or transparent plastic.

The switching element TFT may be a thin film transistor, and the thin film transistor may be configured to include a gate electrode 125, a gate insulating film 130, a semiconductor layer 140, a source electrode 152, and a drain electrode 155. The gate electrode 125, which is a control terminal of the thin film transistor, may be disposed on the first base substrate 110, and may be made of a conductive material. The gate electrode 125 may be branched from the gate line GL. The gate insulating film 130 may be disposed between the gate electrode 125 and the semiconductor layer 140 to insulate them, and may be formed to extend from the display area I to the non-display area II. The semiconductor layer 140, which is a channel layer of the thin film transistor, may be disposed on the gate insulating film 130. The source electrode 152 and the drain electrode 155 may be disposed on the semiconductor layer 140 to be spaced from each other, and may be made of a conductive material. The source electrode 152 is an input terminal of the thin film transistor, and the drain electrode 155 is an output terminal of the thin film transistor. The source electrode 152 and the drain electrode 155 may be branched from the data line DL. Ohmic contact layers (not shown) may be respectively formed between the source electrode 152 and the semiconductor layer 140 and between the drain electrode 155 and the semiconductor layer 140.

The gate line GL may be disposed between the first base substrate 110 and the first electrode 180, and the data line DL may be disposed between the gate line GL and the first electrode 180.

The color filter layer 160 may be formed on the source electrode 152 and the drain electrode 155. The color filter layer 160 may be disposed on the switching element TFT, for example, may be disposed between the switching element TFT and the first electrode 180. The color filter layer 160 may be formed in a region corresponding to each pixel PX in the display area I, wherein the color filter layer 160 includes a first color filter 160-1 and a second color filter 160-2. For example, the first color filter 160-1 and the second color filter 160-2 may be color filters realizing different colors from each other. Each of the first color filter 160-1 and the second color filter 160-2 may be one of a red color filter (R), a green color filter (G), and a blue color filter (B). The first color filter 160-1 and the second color filter 160-2 may be arranged alternately.

The organic film 170 made of an organic material may be formed on the color filter layer 160. The organic film 170 may extend to the non-display area II.

On the organic film 170, the first electrode 180 made of a conductive material may be formed for each pixel PX. The first electrode 180 may be electrically connected with the drain electrode 155 through a contact hole 172 penetrating the organic film 170 and the color filter layer 160. The switching element TFT is electrically connected to the gate line GL and the f electrode 180. The first electrode 180 may be made of indium tin oxide, indium zinc oxide, indium oxide, zinc oxide, tin oxide, gallium oxide, titanium oxide, aluminum, silver, platinum, chromium, molybdenum, tantalum, niobium, zinc, magnesium, an alloy thereof, or a laminate thereof. The first electrode 180 is disposed between the color filter layer 160 and the liquid crystal layer 300.

The first electrode 180 forms an electric field together with the second electrode 250 to control the alignment direction of liquid crystal molecules in the liquid crystal layer 300 disposed therebetween. The first electrode 180 may be a pattern electrode having at least one of a protrusion pattern and a slit pattern, or may be a patternless electrode.

The light-blocking spacer 195 may be disposed on the display substrate SUB1. In an embodiment, the light-blocking spacer 195 may include an area disposed between the first electrode 180 and the second electrode 250, and an area disposed to overlap the switching element TFT. The light-blocking spacer 195 serves as both a spacer for maintaining the thickness of the liquid crystal layer 300 and a black matrix. The light-blocking spacer 195 may be made of a light-blocking material, such as an organic material containing carbon black. The light-blocking material may also be made of a material having predetermined elasticity. The light-blocking spacer 195 serves as both a black matrix and a spacer for maintaining the thickness of the liquid crystal layer 300.

The light-blocking spacer 195, for example, may include a main spacer 195M and a sub spacer 195S. The main spacer 195M is formed to have a height higher than that of the subs spacer 195S, and can serve to maintain the thickness of the liquid crystal layer 300 even when external force is applied to the liquid crystal display device 500. The sub spacer 195S can serve to prevent the elasticity of the main spacer 195M from being destroyed by buffering the external force applied to the main spacer 195M when the external force is stronger than the elasticity of the main spacer 195M. The height difference t1−t2 between the main spacer 195M and the sub spacer 195S may be 0.25 μm to 0.8 μm. For example, when the main spacer 195M has a thickness t1 of 3 μm, the sub spacer 195S may have a thickness t2 of 2.5 μm.

The first liquid crystal alignment layer 190 may include an area disposed between the first electrode 180 and the liquid crystal layer 300 and an area disposed between the light-blocking spacer 195 and the second liquid crystal alignment layer 270. The first liquid crystal alignment layer 190 may include a polymer network composed of polymers of the reactive mesogens, and, for example, may include a polymer network composed of polymers of one or more reactive mesogens of the compound represented by Formula RM1.

The polymer network composed of polymers of the reactive mesogens serves to align the liquid crystal compound molecules 301 at a predetermined pretilt angle with respect to the display substrate SUB1 and the counter display substrate SUB2 even in a state where an electric field is not applied to the first liquid crystal display device 500. The pretilt angle means an angle between the display substrate SUB1 and the director of the liquid crystal compound molecules 301 and an angle between the counter display substrate SUB2 and the director of the liquid crystal compound molecules 301.

Although not shown in the drawings, the first liquid crystal alignment layer 190 includes a polyimide alignment base layer and the polymer network composed of polymers of the reactive mesogens, and may further include an alignment stabilizing layer formed on the polyimide alignment base layer. However, since the polyimide alignment base layer may be emitted, the first liquid crystal alignment layer 190 may not include both the polyimide alignment base layer and the alignment stabilizing layer.

The second base substrate 210 is a base substrate of the counter display substrate SUB2, and may be made of a transparent insulating material, such as glass or transparent plastic.

The second electrode 250 may be directly disposed on the second base substrate 210. The second electrode 250 may be a pattern electrode having at least one of a protrusion pattern and a slit pattern, or may be a patternless electrode. The second electrode 250 may be made of indium tin oxide, indium zinc oxide, indium oxide, zinc oxide, tin oxide, gallium oxide, titanium oxide, aluminum, silver, platinum, chromium, molybdenum, tantalum, niobium, zinc, magnesium, an alloy thereof, or a laminate thereof.

The second liquid crystal alignment layer 270 may be directly disposed on the second electrode 250. The second liquid crystal alignment layer 250 may include an area disposed between the second electrode 250 and the liquid crystal layer 300 and an area disposed between the second electrode 250 and the first liquid crystal alignment layer 190. The second liquid crystal alignment layer 270 may extend to the non-display area II as well as the display area I. The second liquid crystal alignment layer 270 may include a polymer network composed of polymers of the reactive mesogens, and, for example, may include a polymer network composed of polymers of one or more reactive mesogens of the compound represented by Formula RM1.

The polymer network composed of polymers of the reactive mesogens serves to align the liquid crystal compound molecules 301 at a predetermined pretilt angle with respect to the display substrate SUB1 and the counter display substrate SUB2 even in a state where an electric field is not applied to the first liquid crystal display device 500. The pretilt angle means an angle between the display substrate SUB1 and the director of the liquid crystal compound molecules 301 and an angle between the counter display substrate SUB2 and the director of the liquid crystal compound molecules 301.

Although not shown in the drawings, the second liquid crystal alignment layer 270 includes a polyimide alignment base layer and the polymer network composed of polymers of the reactive mesogens, and may further include an alignment stabilizing layer formed on the polyimide alignment base layer. However, since the polyimide alignment base layer may be emitted, the second liquid crystal alignment layer 270 may not include both the polyimide alignment base layer and the alignment stabilizing layer.

Although not shown in the drawing, the first liquid crystal display device 500 may further include a backlight assembly (not shown) disposed on the rear surface of the display substrate SUB1 to provide light to the liquid crystal layer 300.

The backlight assembly, for example, may include a light guide plate (not shown), a light source (not shown), a reflection member (not shown), and an optical sheet (not shown).

The light guide plate (LGP) serves to change the path of light emitted from the light source toward the liquid crystal layer 300, and may include a light incidence surface provided to allow the light emitted from the light source to be applied thereto, and a light emission surface emitting the incident light toward the liquid crystal layer 300. The light guide plate may be made of a material having a predetermined refractive index, such as polymethyl methacrylate (PMMA) or polycarbonate (PC), which is one of light transmissive materials, but the present disclosure is not limited thereto.

Since the light incoming onto one side or both sides of the light guide plate made of such a material has an angle within the critical angle, the light is transmitted to the inside of the light guide plate. Further, when the light incomes to the upper surface or lower surface of the light guide plate, the angle of the light exceeds the critical angle, so that the light is not emitted to the outside of the light guide plate, and is uniformly transmitted in the light guide plate.

A scattering pattern may be formed on any one of the upper and lower surfaces of the light guide plate, for example, on the upper surface facing the light emission surface, such that the guided light is emitted to the upper surface thereof. That is, the scattering pattern may be printed with ink on one side of the light guide plate such that the light transmitted in the light guide plate is emitted to the upper surface thereof. Such a scattering pattern may be formed by printing with ink, but is not limited thereto. Further, the light guide plate may be provided with fine grooves or protrusions, and may be modified as desired.

The reflection member may further be provided between the light guide plate and the bottom of the storage member. The reflection member serves to reflect the light emitted to the lower surface of the light guide plate, that is, the opposite surface facing the light emission surface and supply the reflected light to the light guide plate. The reflection member may be fabricated in the form of a film, but the present disclosure is not limited thereto.

The light source may be disposed to face the light incidence surface of the light guide plate. The number of light sources can be appropriately changed as needed. For example, only one side of the light guide plate can be provided with one light source, and three or more light sources can also be provided corresponding to three or more sides of four sides of the light guide plate. Further, a plurality of light source can be provided corresponding to any one of sides of the light guide plate. As described above, the side light type light source has been described as an example, but other examples thereof include a direct type light source and a surface shape type light source.

The light source may be a white LED emitting white light, and may also be a plurality LEDs emitting red light (R), green light (G), and blue light (B), respectively. When the plurality of light sources are realized as the plurality LEDs emitting red light (R), green light (G), and blue light (B), respectively, and when these light sources turn on at once, white light can be realized by color mixing.

Figure 5:
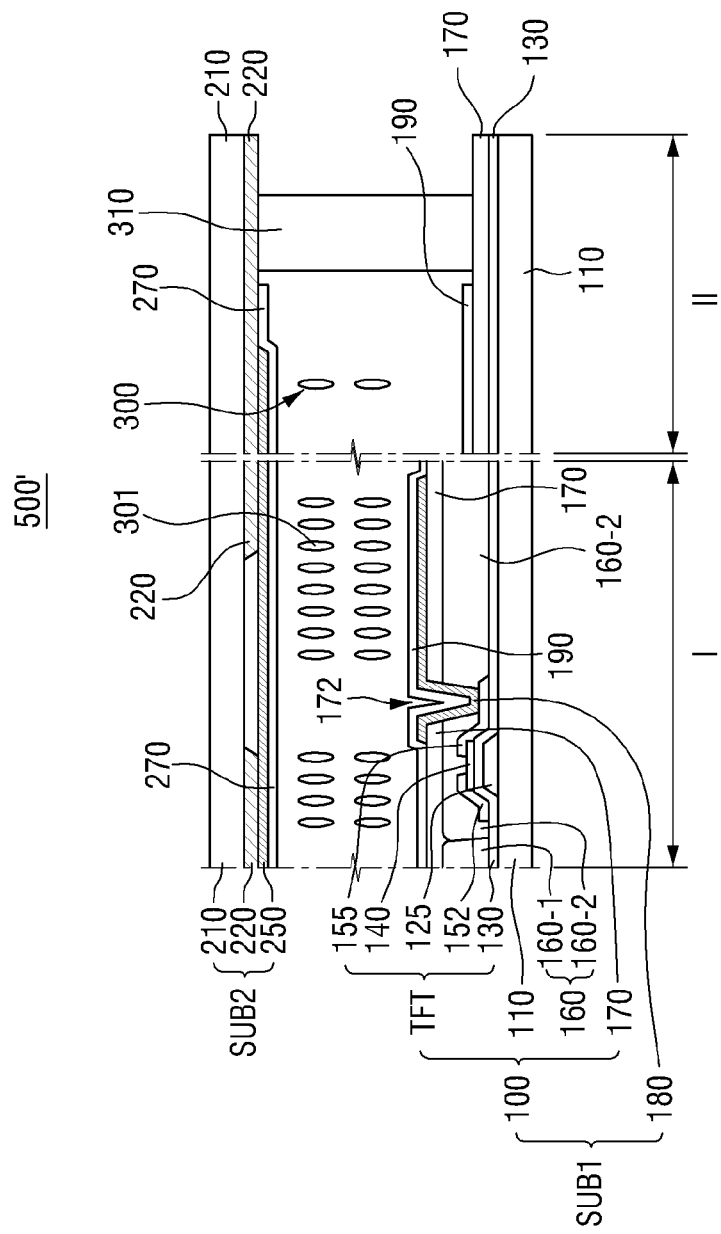
FIG. 5 is a schematic cross-sectional view of the initial state of a second liquid crystal display device, to which an electric field is not applied.

FIG. 5 is a schematic cross-sectional view of the initial state of a second liquid crystal display device 500', to which an electric field is not applied. Hereinafter, the second liquid crystal display device 500' will be described except for the portions different from the first liquid crystal display device (500 of FIG. 2).

The second liquid crystal display device 500' is different from the first liquid crystal display device 500 of FIG. 2 in that a counter display substrate SUB2 is configured to include a second base substrate 210, a light-blocking pattern 220, and a second electrode 250. The counter display substrate SUB2 of the first liquid crystal display device 500 of FIG. 2 is configured to include the second base substrate 210 and the second electrode 250. The second liquid crystal display device 500' does not include the light-blocking spacer (195 of FIG. 2). Although not shown, the second liquid crystal display device 500' may further include a column spacer (not shown) for maintaining the thickness of the liquid crystal layer 300, and the spacer may be made of a light transmissive material. The display substrate SUB1 and the counter display substrate SUB2 may be attached to each other by a seal line 310 made of a sealant. The seal line 310, which is a peripheral portion of the display substrate SUB1 and the counter display substrate SUB2, may be located on the non-display area (II). The seal line 310 surrounds the display area (I).

As described above, since the compound represented by Formula P above has poor stability to ultraviolet rays of about 260 nm to 380 nm, the reliability of the second liquid crystal display device 500' can be improved by partially or entirely replacing the compounds represented by Formula P above with at least one of the compounds represented by the Formula 1-A.

Figure 6:
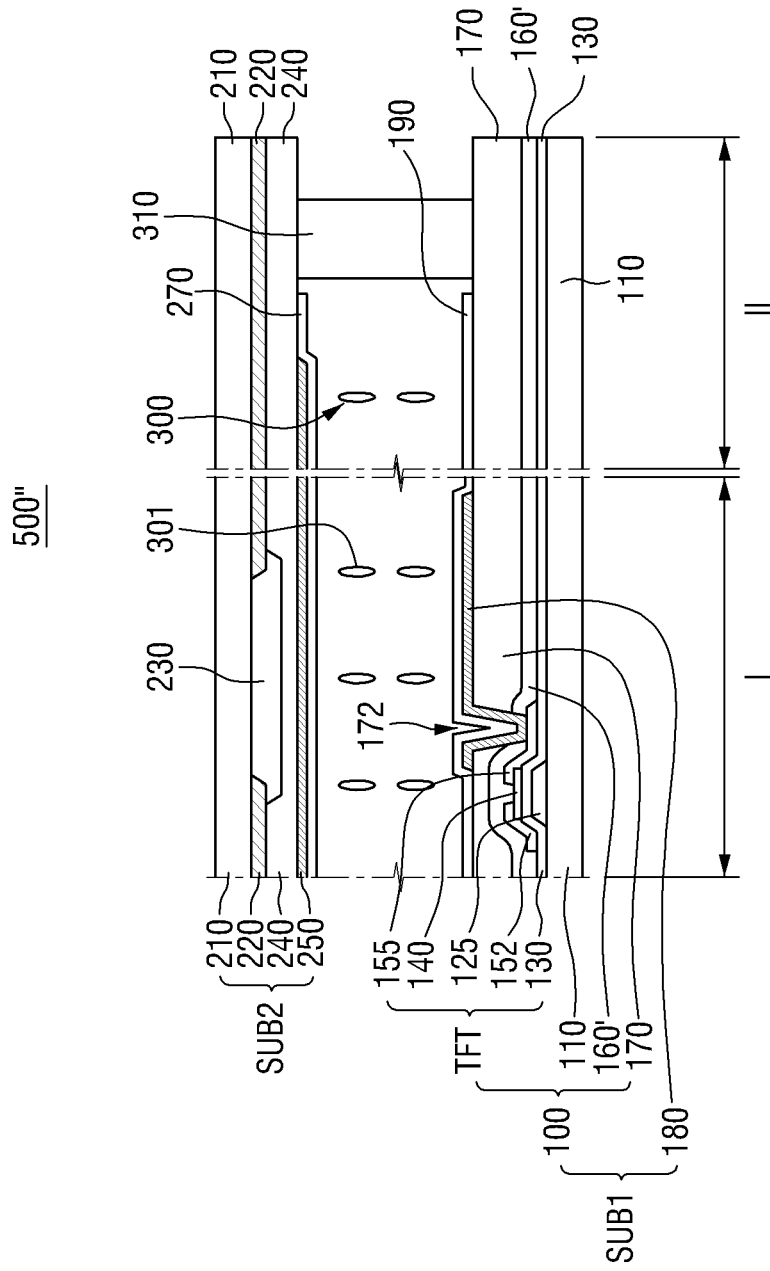
FIG. 6 is a schematic cross-sectional view of the initial state of a third liquid crystal display device, to which an electric field is not applied.

FIG. 6 is a schematic cross-sectional view of the initial state of a third liquid crystal display device 500", to which an electric field is not applied. Hereinafter, the third liquid crystal display device 500" will be described except for the portions different from the first liquid crystal display device (500 of FIG. 2).

The third liquid crystal display device 500" is different from the first liquid crystal display device 500 of FIG. 2 in that the switching element array substrate 100 is configured to include a first base substrate 110, a switching element TFT disposed on the first base substrate 110, an inorganic film 160' disposed on the switching element TFT, and an organic film 170 disposed on the inorganic film 160'. The switching element array substrate 100 of the first liquid crystal display device 500 of FIG. 2, for example, is configured to include the first base substrate 110, the switching element TFT disposed on the first base substrate 110, the color filter layer 160 disposed on the switching element TFT, and the organic film 170 disposed on the color filter layer 160.

The third liquid crystal display device 500" is different from the first liquid crystal display device 500 of FIG. 2 in that a counter display substrate SUB2 is configured to include a second base substrate 210, a light-blocking pattern 220, an overcoat film 240, and a second electrode 250. The counter display substrate SUB2 of the first liquid crystal display device 500 of FIG. 2 is configured to include the second base substrate 210 and the second electrode 250.

The third liquid crystal display device 500" does not include the light-blocking spacer (195 of FIG. 2). Although not shown, the third liquid crystal display device 500" may further include a column spacer (not shown) for maintaining the thickness of the liquid crystal layer 300, and the spacer may be made of a light transmissive material. The display substrate SUB1 and the counter display substrate SUB2 may be attached to each other by a seal line 310 made of a sealant. The seal line 310, which is a peripheral portion of the display substrate SUB1 and the counter display substrate SUB2, may be located on the non-display area (II). The seal line 310 surrounds the display area (I).

As described above, since the compound represented by Formula P above has poor stability to ultraviolet rays of about 260 nm to 380 nm, the reliability of the third liquid crystal display device 500″ can be improved by partially or entirely replacing the compounds represented by Formula P above with at least one of the compounds represented by the Formula 1-A.

While exemplary embodiments have been shown and described above, it will be apparent to those skilled in the art that modifications and variations could be made without departing from the spirit and scope of the disclosure as defined by the appended claims. The exemplary embodiments should be considered in a descriptive sense only and not for purposes of limitation.

What is claimed is:

1. A liquid crystal composition, consisting of:
   at least one compound represented by Formula 1-A,
   at least one compound represented by Formulae 2-1 to 2-17, and
   at least one reactive mesogen represented by Formula RM:

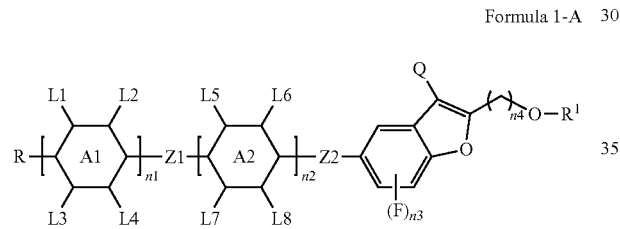

Formula 1-A wherein, in the Formula 1-A,
R—* is *—H, *—F, *Cl—, *—Br, *—I, a $C_{1-12}$ alkyl group, or a cyano group,
$R^1$—* is a $C_{1-12}$ alkyl group;
Q-* is *—H or a $C_{1-5}$ alkyl group;
*—Z1-* and *—Z2-* are the same or different and are each independently *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_m$—* wherein m is an integer of 1 to 5, *—CH=CH—*, *—CF=CF—*, *—CH=CF—*, *—CF=CH—*, *—C≡C—*, *—CH=CHCH$_2$O—*, or a single bond;

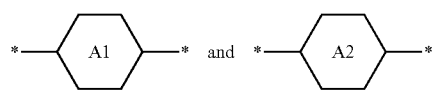

are the same as or different and are each independently

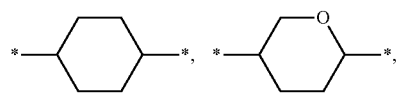

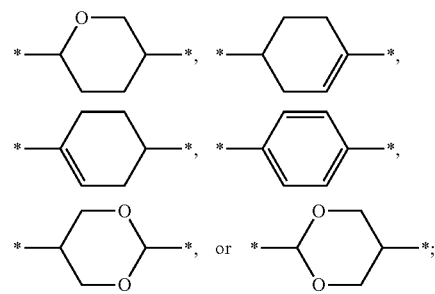

n1 and n2 are each independently an integer of 0 to 3; and n3 is an integer of 1 to 3;

n4 is an integer of 1 or 2; and

L1-*, L2-*, L3-*, L4-*, L5-*, L6-*, L7-*, and L8-* are the same or different and are each independently *—H, *—F, *Cl—, *—OCF$_3$, *—CF$_3$, *—CH$_2$F, or *—CHF$_2$,

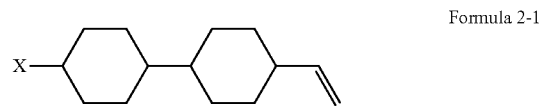

Formula 2-1

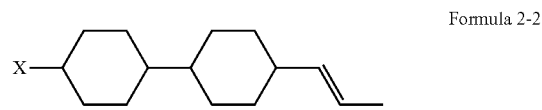

Formula 2-2

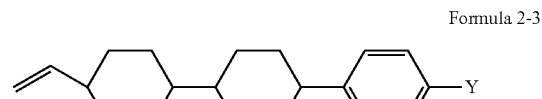

Formula 2-3

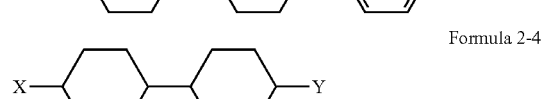

Formula 2-4

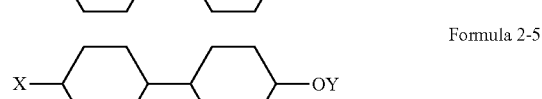

Formula 2-5

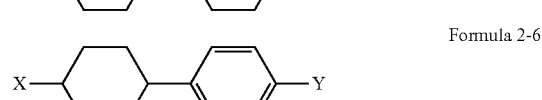

Formula 2-6

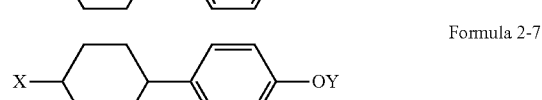

Formula 2-7

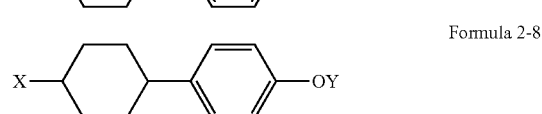

Formula 2-8

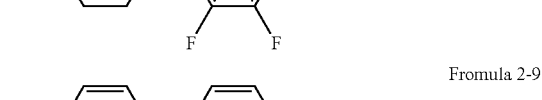

Fromula 2-9

-continued

Formula 2-10
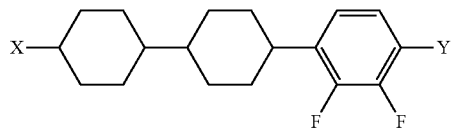

Formula 2-11
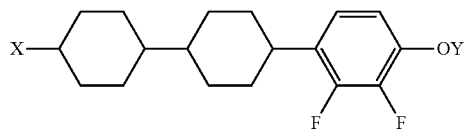

Formula 2-12
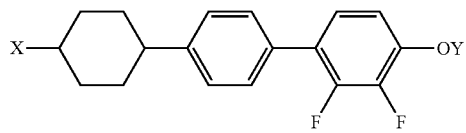

Formula 2-13
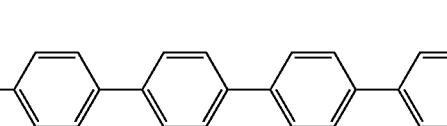

Formula 2-14
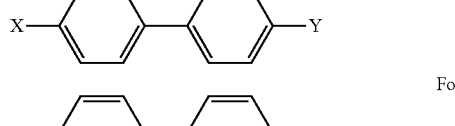

Formula 2-15
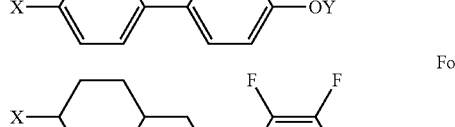

Formula 2-16
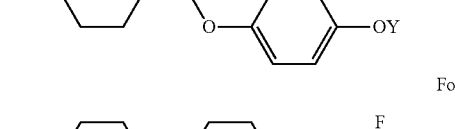

Formula 2-17
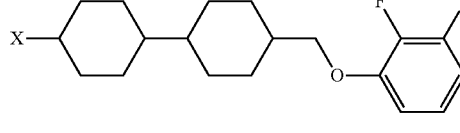

wherein, in the Formulae 2-1 to 2-17,

X—* and Y—* are each independently a $C_{1-5}$ alkyl group,

P1-SP1-MG-SP2-P2   Formula RM wherein, in the Formula RM,

P1-* and P2-* are the same or different and are each independently

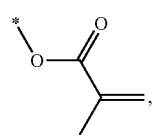 , 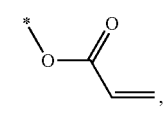 ,  ,

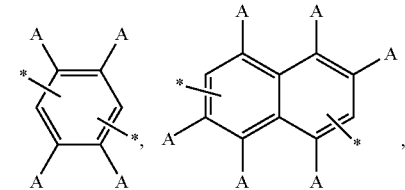

*—SP1—* is

*—(L—Z—L—Ar)$_a$—L—* wherein a is an integer of 0 to 2;

*—SP2—* is

*—L—(Ar—L—Z—L)$_b$—* wherein b is integer of 0 to 2;

*-MG-* is

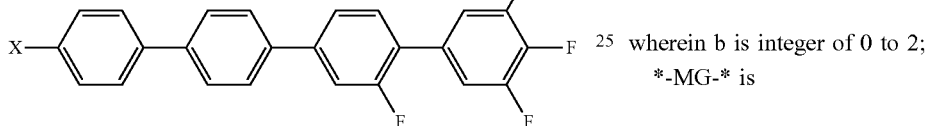

wherein, in the

*—(L—Z—L—Ar)$_a$—L—* and
*—L—(Ar—L—Z—L)$_b$—*,

*-L-* is *—(CH$_2$)$_c$—*, wherein c is an integer of 1 to 10,
*—(CH$_2$)$_d$—O—*, wherein d is an integer of 1 to 10,

*—O—C(=O)—*, *—N(H)—*, *—N(H)—C(=O)—*,

*—CH=CH—*, or *—C≡C—*,

*—Z—* is *—(CH$_2$)$_e$—* wherein e is an integer of 0 to 12, and

*—Ar—* is

-continued

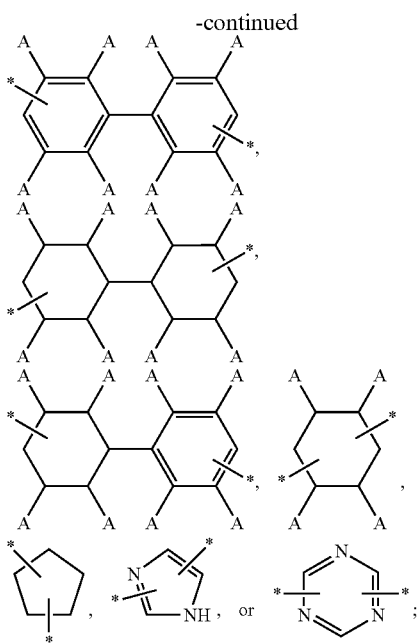

and
wherein, in the

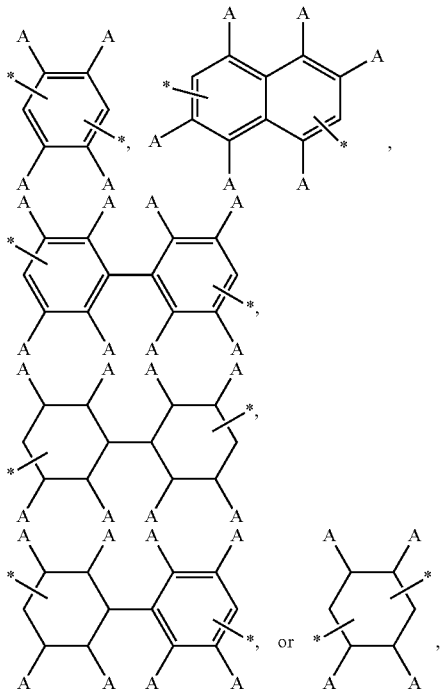

A-* is H—*, a $C_{1-10}$ alkyl group, F—*, Cl—*, Br—*, I—*, *—OH, *—NH$_2$, or CN—*, wherein the content of the at least one compound represented by Formula 1-A is about 1 percent by weight to about 10 percent by weight based on the total weight of the liquid crystal composition, wherein "about" means within 5% of the stated value, and wherein the liquid crystal composition has a refractive index anisotropy (Δn) of 0.10 to 0.12, a dielectric anisotropy (Δε) of −3.0 to −3.6, and a rotational viscosity (γ1, 20° C.) of 95 millipascal seconds (mPa·s) to 140 millipascal seconds (mPa·s)

wherein the symbol "*" is defined as a bonding site in which adjacent elements are covalently bonded to each other.

2. The liquid crystal composition of claim 1, wherein

Q-* is *—H, and n4 is an integer of 1 wherein the symbol "*" is defined as a bonding site in which adjacent elements are covalently bonded to each other.

3. The liquid crystal composition of claim 1, wherein

Q-* is *—H, and n3 is an integer of 2 wherein the symbol "*" is defined as a bonding site in which adjacent elements are covalently bonded to each other.

4. The liquid crystal composition of claim 1, wherein

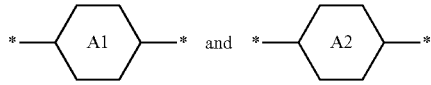

are the same or different and are each independently

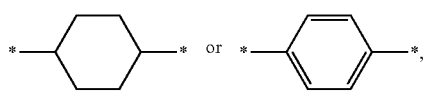

and

*—Z1-* and *—Z2-* are each a single bond wherein the symbol "*" is defined as a bonding site in which adjacent elements are covalently bonded to each other.

5. The liquid crystal composition of claim 1, wherein the at least one compound represented by Formula 1-A is a compound represented by Formula 1-B:

Formula 1-B

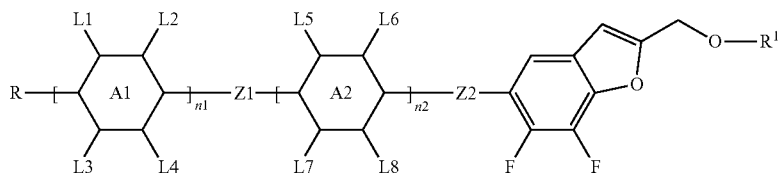

wherein, in the Formula 1-B,

A1, A2, L1-*, L2-*, L3-*, L4-*, L5-*, L6-*, L7-*, L8-*, R—*, R¹—*, *—Z1-*, *—Z2-*, n1, and n2 are the same as in the Formula 1-A wherein the symbol "*" is defined as a bonding site in which adjacent elements are covalently bonded to each other.

6. The liquid crystal composition of claim 1, wherein the at least one compound represented by Formula 1-A is a compound represented by Formulae 1-1 to 1-4:

Formula 1-1

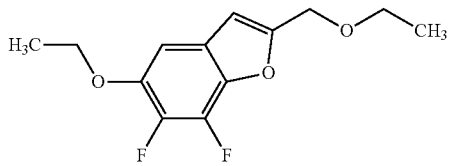

Formula 1-2

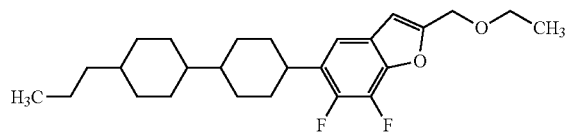

Formula 1-3

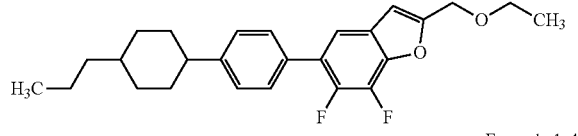

Formula 1-4

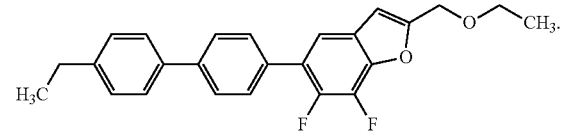

7. A liquid crystal display device, comprising:
a display substrate comprising a first base substrate, a switching element disposed on the first base substrate, and a first electrode disposed on the switching element;
a counter display substrate comprising a second base substrate and a second electrode disposed on the second base substrate and facing the display substrate; and
a liquid crystal layer consists of at least one compound represented by Formula 1-A, at least one compound represented by Formulae 2-1 to 2-17, and at least one reactive mesogen represented by Formula RM, wherein the liquid crystal layer is disposed between the display substrate and the counter display substrate:

Formula 1-A

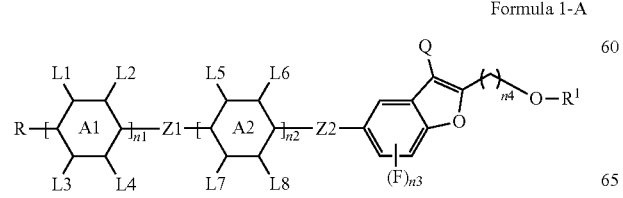

wherein, in the Formula 1-A,

R—* is *—H, *—F, *—Cl, *—Br, *—I, a $C_{1-12}$ alkyl group, or a cyano group, $R^1$—* is a $C_{1-12}$ alkyl group;

Q-* is *—H or a C1s alkyl group;

*—Z1-* and *—Z2-* are the same or different and are each independently *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_m$—* wherein m is an integer of 1 to 5, *—CH═CH—*, *—CF═CF—*, *—CH═CF—*, *—CF═CH—*, *—C≡C—*, *—CH═CHCH$_2$O—*, or a single bond;

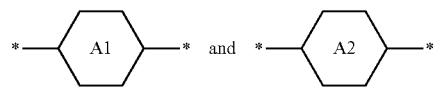

are the same or different and are each independently

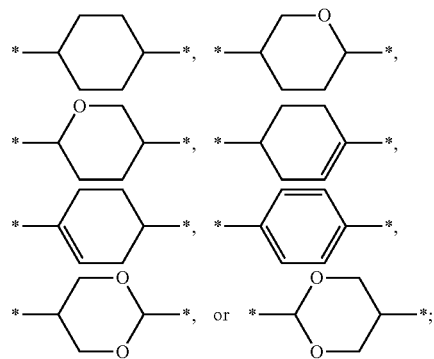

n1 and n2 are each independently an integer of 0 to 3;

n3 is an integer of 1 to 3;

n4 is an integer of 1 or 2; and

L1-*, L2-*, L3-*, L4-*, L5-*, L6-*, L7-*, and L8-* are the same or different and are each independently *—H, *—F, *—Cl, *—OCF$_3$, *—CF$_3$, *—CH$_2$F, or *—CHF$_2$, Formula 2-1

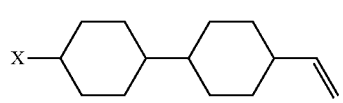

Formula 2-2

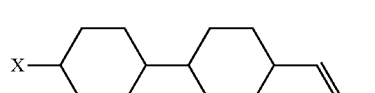

Formula 2-3

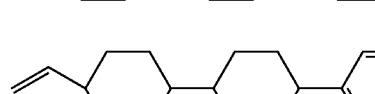

Formula 2-4

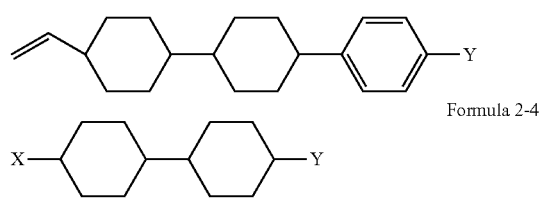

45
-continued

Formula 2-5
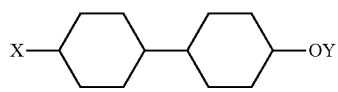

Formula 2-6
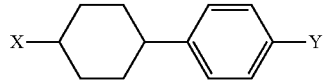

Formula 2-7
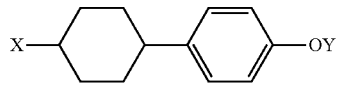

Formula 2-8
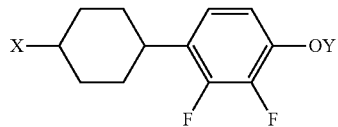

Formula 2-9
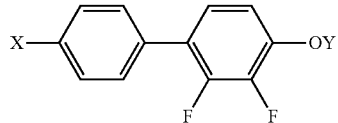

Formula 2-10
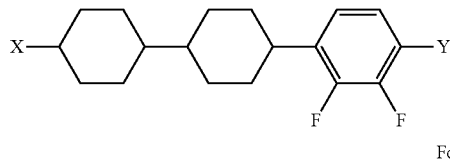

Formula 2-11
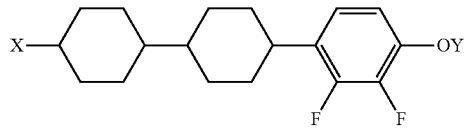

Formula 2-12
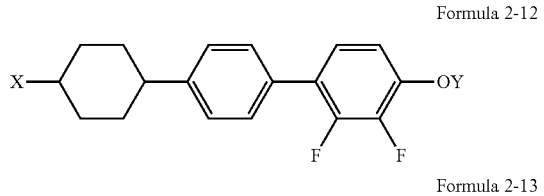

Formula 2-13
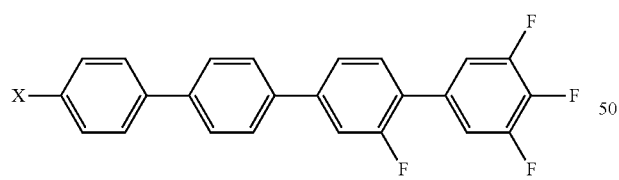

Formula 2-14
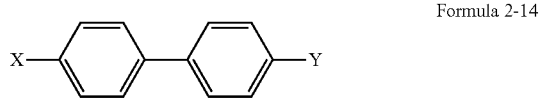

Formula 2-15
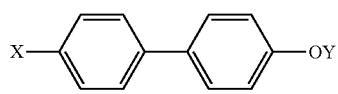

Formula 2-16
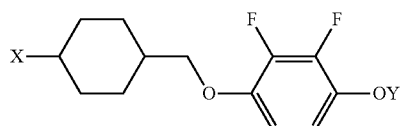

46
-continued

Formula 2-17
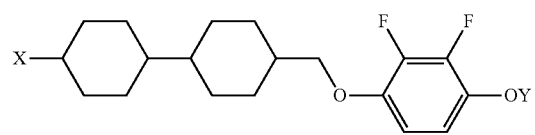

wherein, in the Formulae 2-1 to 2-17,
X—* and Y—* are each independently a $C_{1-5}$ alkyl group, P1-SP1-MG-SP2-P2    Formula RM wherein, in the Formula RM,
P1-* and P2-* are the same or different and are each independently

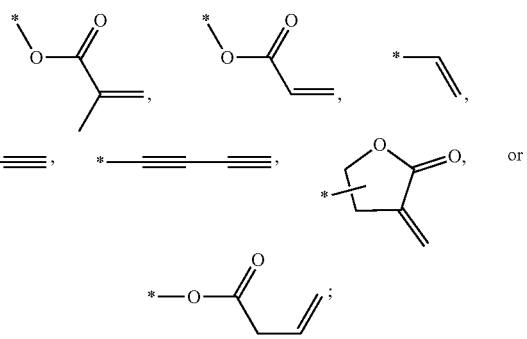

*—SP1-* is

*—[L—Z—L—Ar]$_a$—L—* wherein a is an integer of 0 to 2;
*—SP2-* is

*—[L—Ar—L—Z—L]$_b$—* wherein b is integer of 0 to 2;
*-MG-* is

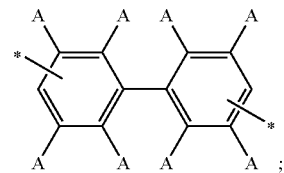

wherein, in the

*—[L—Z—L—Ar]$_a$—L—*  and
*—[L—Ar—L—Z—L]$_b$—*,

*-L-* is *—(CH$_2$)$_c$—*, wherein c is an integer of 1 to 10,
*—(CH$_2$)$_d$—O—*, wherein d is an integer of 1 to 10,

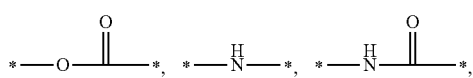

*—CH=CH—*, or *—C≡C—*,

*—Z—* is *—(CH$_2$)$_e$—* wherein e is an integer of 0 to 12, and

*—Ar—* is

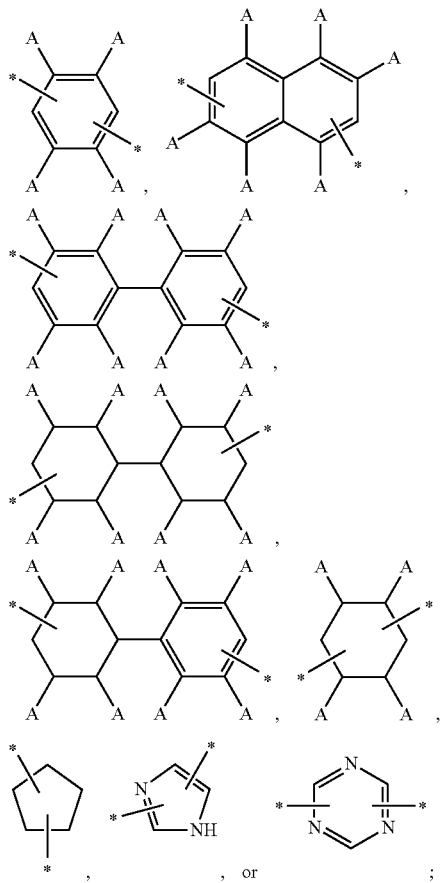

and wherein, in the

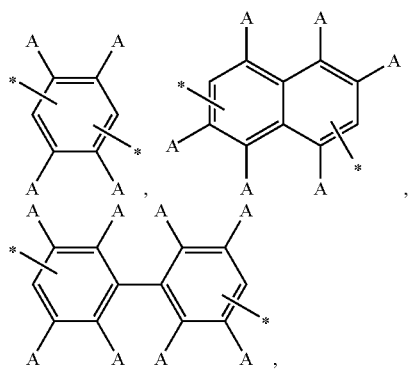

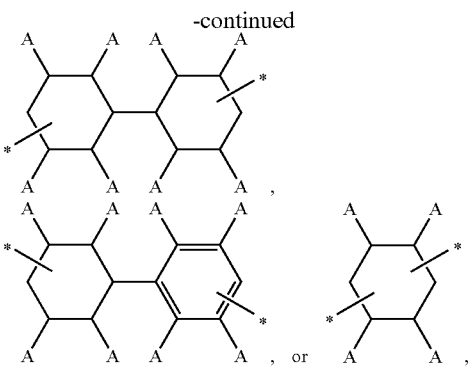

A-* is H—*, a C$_{1-10}$ alkyl group, F—*, Cl—*, Br—*, I—*, *—OH, *—NH$_2$, or CN—*, wherein the content of the at least one compound represented by Formula 1-A is about 1 percent by weight to about 10 percent by weight based on the total weight of the liquid crystal composition, wherein "about" means within 5% of the stated value, and wherein the liquid crystal layer has a refractive index anisotropy (Δn) of 0.10 to 0.12, a dielectric anisotropy (Δε) of −3.0 to −3.6, and a rotational viscosity (γ1, 20° C.) of 95 millipascal seconds (mPa·s) to 140 millipascal seconds (mPa·s)

wherein the symbol "*" is defined as a bonding site in which adjacent elements are covalently bonded to each other.

8. The liquid crystal display device of claim 7, wherein Q-* is *—H, and n4 is an integer of 1 wherein the symbol "*" is defined as a bonding site in which adjacent elements are covalently bonded to each other.

9. The liquid crystal display device of claim 7, wherein Q-* is *—H, and n3 is an integer of 2 wherein the symbol "*" is defined as a bonding site in which adjacent elements are covalently bonded to each other.

10. The liquid crystal display device of claim 7, wherein

and are the same or different and are each independently

and

*—Z1-* and *—Z2-* are each a single bond wherein the symbol "*" is defined as a bonding site in which adjacent elements are covalently bonded to each other.

11. The liquid crystal display device of claim 7, wherein the at least one compound represented by Formula 1-A is a compound represented by Formula 1-B:

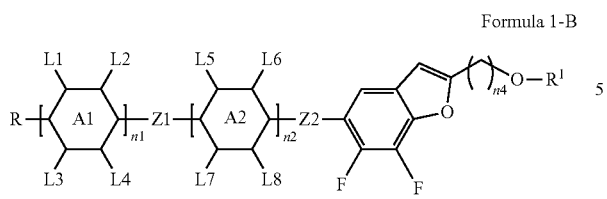

Formula 1-B wherein, in the Formula 1-B,

A1, A2, L1-*, L2-*, L3-*, L4-*, L5-*, L6-*, L7-*, L8-*, R—*, R¹—*, n1, and n2 are the same as in the Formula 1-A wherein the symbol "*" is defined as a bonding site in which adjacent elements are covalently bonded to each other.

12. The liquid crystal display device of claim 7, further comprising:

a liquid crystal alignment layer comprising a polymer of the reactive mesogen, wherein the liquid crystal alignment layer is disposed between the liquid crystal layer and at least one of the display substrate and the counter display substrate.

13. The liquid crystal display device of claim 7, wherein the at least one compound represented by Formula 1-A is a compound represented by Formulae 1-1 to 1-4:

Formula 1-1

Formula 1-2

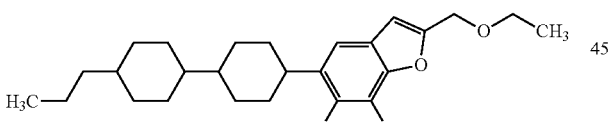

Formula 1-3

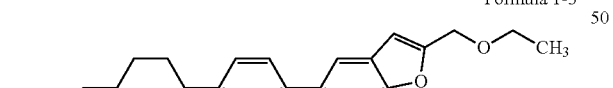

Formula 1-4

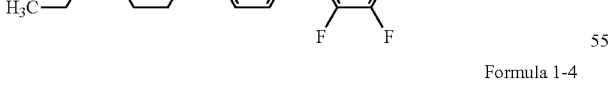

14. The liquid crystal composition of claim 6, wherein the reactive mesogen is at least one compound represented by Formula RM1:

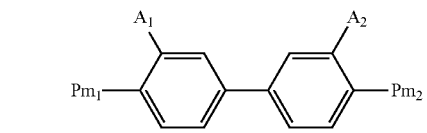

wherein, in the Formula RM1,

Pm$_1$—* and Pm$_2$—* are each independently

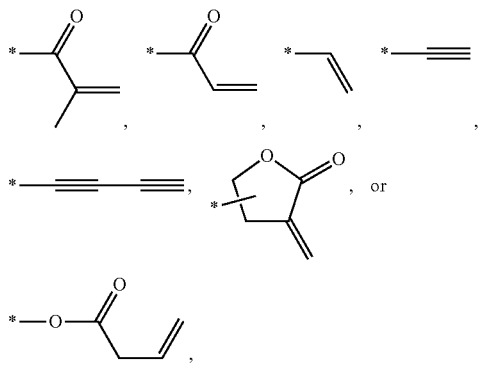

and

A$_1$-* and A$_2$-* are each independently *—H, *—F, *Cl, *—Br, *—I, *—OH, *—NH$_2$, or *—CN wherein the symbol "*" is defined as a bonding site in which adjacent elements are covalently bonded to each other.

15. The liquid crystal display device of claim 13, wherein the reactive mesogen is at least one compound represented by Formula RM1:

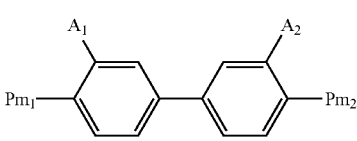

wherein, in the Formula RM1,

Pm$_1$—* and Pm$_2$—* are each independently

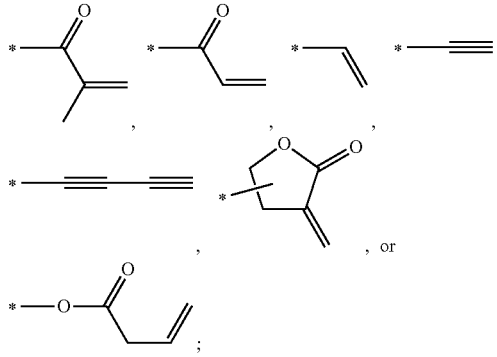

and
$A_1$-* and $A_2$-* are each independently *—H, *—F, *Cl, *—Br, *—I, *—OH, *—NH$_2$, or *—CN
wherein the symbol "*" is defined as a bonding site in which adjacent elements are covalently bonded to each other.

* * * * *